(12) United States Patent
Ahearn et al.

(10) Patent No.: US 9,709,564 B2
(45) Date of Patent: Jul. 18, 2017

(54) ANTI-LYMPHOCYTE AUTOANTIBODIES AS DIAGNOSTIC BIOMARKERS

(71) Applicant: Allegheny-Singer Research Institute, Pittsburgh, PA (US)

(72) Inventors: Joseph M. Ahearn, Wexford, PA (US); Chau-Ching Liu, Pittsburgh, PA (US); Susan M. Manzi, Wexford, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 0 days.

(21) Appl. No.: 14/821,670

(22) Filed: Aug. 7, 2015

(65) Prior Publication Data

US 2016/0041164 A1 Feb. 11, 2016

Related U.S. Application Data

(60) Provisional application No. 62/035,073, filed on Aug. 8, 2014.

(51) Int. Cl.
| | | |
|---|---|---|
| *G01N 33/564* | (2006.01) | |
| *G01N 33/536* | (2006.01) | |
| *G01N 33/50* | (2006.01) | |
| *G01N 33/68* | (2006.01) | |

(52) U.S. Cl.
CPC ......... *G01N 33/564* (2013.01); *G01N 33/505* (2013.01); *G01N 33/5047* (2013.01); *G01N 33/5052* (2013.01); *G01N 33/5055* (2013.01); *G01N 33/536* (2013.01); *G01N 33/6854* (2013.01); *G01N 2333/7051* (2013.01); *G01N 2333/70514* (2013.01); *G01N 2333/70517* (2013.01); *G01N 2800/104* (2013.01); *G01N 2800/7095* (2013.01)

(58) Field of Classification Search
CPC ............ G01N 33/564; G01N 33/5055; G01N 33/505; G01N 33/5052; G01N 33/5047; G01N 33/536; G01N 33/6854; G01N 2800/7095; G01N 2800/104; G01N 2333/70514; G01N 2333/7051; G01N 2333/70517

See application file for complete search history.

(56) References Cited

U.S. PATENT DOCUMENTS

| | | | |
|---|---|---|---|
| 7,585,640 B2 * | 9/2009 | Ahearn | G01N 33/564 435/287.2 |
| 9,075,069 B2 * | 7/2015 | Weber | G01N 33/6854 |

FOREIGN PATENT DOCUMENTS

| | | |
|---|---|---|
| WO | 2014020357 A1 | 2/2014 |
| WO | WO2014093268 | 6/2014 |
| WO | WO2014124098 | 8/2014 |

OTHER PUBLICATIONS

Liu et al. Complement C4d deposition on T lymphocytes: Mechanisms and significance in systemic lupus erythematosus (SLE). Molecular Immunology 44: 147-266 (2007).*

(Continued)

*Primary Examiner* — Gail R Gabel
(74) *Attorney, Agent, or Firm* — Fox Rothschild LLP

(57) ABSTRACT

Provided are methods, systems, and kits for diagnosing or monitoring systemic lupus erythematosus in an individual. In particular aspects, in a blood sample containing white blood cells from the individual, autoantibodies deposited on or contacting with the surface of a T lymphocyte in the sample are quantitated.

22 Claims, 14 Drawing Sheets

(56) References Cited

OTHER PUBLICATIONS

Reininger et al. T helper cell subsets in the pathogenesis of systemic lupus erythematosus. Ann Med Interne 147 (7): 467-471 (1996) (Abstract).*

Liu et al. Lymphocyte-bound complement activation products as biomarkers for diagnosis of systemic lupus erythematosus. Clinical and Translational Science—CTS: 2 (4): 300-308 (Aug. 1, 2009).*

Liu, Chau-Ching et al. Complement C4d deposition on circulating blood cells: Mechanisms and implication in systemic lupus erythematosus (SLE). Molecular Immunology: 47 (13): Suppl. 4, pp. 2286 (Aug. 2010).*

Liu, Chau-Ching et al. Lymphocyte-bound complement activation products (LB-CAP) as biomarkers for SLE. Lupus. vol. 19, Supp. Suppl. 1, pp. 54. (Jun. 2010).*

Agarwal et al. Reticulocytes bearing C4d in Patients Hospitalized for Acute Infections. Arthritis and Rheumatism 60 (Abstract Supplement Oct. 2009).*

Liu et al., "Complement C4d deposition on T lymphocytes: Mechanisms and significance in systemic lupus erythematosus (SLE)", Molecular Immunology, Pergamon, GB, vol. 44, No. 1-3, p. 206, Jan. 1, 2007.

Ahearn et al., "The lupus biomarker odyssey: one experience.", Methods in Molecular Biology (Clifton, N.J) 2014, vol. 1134, pp. 17-35, Jan. 22, 2014.

Liu et al., "Biomarkers in systemic lupus erythematosus; challenges and prospects for the future.", Therapeutic Advances in Musculosketal Disease, vol. 5, No. 4, pp. 210-233, Aug. 1, 2013.

Liu et al., "Lymphocyte-bound complement activation products as biomarkers for diagnosis of systemic lupus erythematosus" Clinical and Translational Science—CTS, Wiley-Blackwell Publishing, Inc. US, vol. 2, No. 4, Aug. 1, 2009, pp. 300-308, retrieved on Jul. 31, 2009.

Li et al., "Antilymphocyte Antibodies in Systemic Lupus Erythematosus: Association with Disease Activity and Lymphopenia", Journal of Immunology Research, vol. 2014, Art ID 672126, 6 pages, Published Apr. 17, 2014.

Winchester et al., "Analyses of Lymphocytes from Patients with Rheumatoid Arthritis and Systemic Lupus Erythematosus", The Journal of Clinical Investigation, vol. 54, Nov. 1974, pp. 1082-1092.

Bentwich et al., "Specific Properties of Human B and T Lymphocytes and Alterations in Disease", Transplant. Rev. (1973), vol. 16, 29-50.

Liu et al., "Antilymphocyte autoantibodies generate T cell-C4d signatures in systemic lupus erythematosus", Transl Res. Dec. 2014; 164(6): 496-507. Doi: 10.1016/j. trsl. 2014.07.007.Epub Aug. 7, 2014.

Agarwal S. et al., "Arthritis & Rheumatism, vol. 60, Oct. 2009 Abstract Supplement", The 2009 ACR/ARHP Annual Scientific Meeting, Philadelphia Oct. 16-21, 2009.

Palter, Jenny Thorn, "AVISE(TM) SLE: Improving Diagnosis, Improving Care", Nov. 1, 2012.

* cited by examiner

ANTI-LYMPHOCYTE AUTOANTIBODIES AS DIAGNOSTIC BIOMARKERS

CROSS-REFERENCE TO RELATED APPLICATION

This application claims the benefit of U.S. Provisional Patent Application No. 62/035,073, filed Aug. 8, 2014, titled "Methods of Using Anti-Lymphocyte Autoantibodies as Indicators for Systemic Lupus Erythematosus", the disclosure of which is hereby incorporated by reference herein in its entirety.

STATEMENT OF FEDERALLY SPONSORED RESEARCH

This invention was made with government support under (i) contract RO1 AI077591, awarded by the National Institutes of Health, and (ii) Research Grant W81XWH-06-2-0038, awarded by the U.S. Department of Defense. The government has certain rights in the invention.

BACKGROUND

Systemic Lupus Erythematosus (SLE), the prototypic systemic autoimmune disease, is characterized by myriad immune abnormalities including excessive autoantibody production, activation of the complement system, lymphocyte dysfunction, and lymphopenia. Upon activation of the complement system, proteolytic cleavage of C3 and C4 results ultimately in the generation of C3d and C4d fragments that contain the highly reactive thioester moiety and can bind covalently to the surfaces of pathogens, cells, or immune complexes. The present inventors have recently reported that significant levels of C4d are present specifically on the surfaces of erythrocytes, reticulocytes, platelets, and lymphocytes of patients with SLE. A recent multicenter study validated cell-bound complement activation products (CB-CAPs) as diagnostic biomarkers for lupus and additional reports have demonstrated their significant potential as biomarkers of lupus disease activity and stratification.

In addition to their roles as lupus biomarkers, CB-CAPs have been shown to confer functional abnormalities to circulating cells such as erythrocytes and T lymphocytes, suggesting a role in lupus pathogenesis. Elucidation of the cellular and molecular events whereby CB-CAPs are generated may lead to identification of potential therapeutic targets either by preventing, disrupting, or neutralizing the downstream effects of CB-CAP generation. One of the most intriguing potential links between CB-CAPs and lupus pathogenesis is the longstanding yet poorly understood observation that patients with SLE harbor circulating anti-lymphocyte antibodies.

Anti-Lymphocyte antibodies (ALA) in patients with SLE, particularly those specific for T cells, were discovered in the 1970's. Since then, numerous efforts have been made to characterize these ALA. However, their role in disease pathogenesis has remained uncertain. Two primary types of anti-T cell antibodies in SLE have been described previously. First, cold reactive IgM antibodies, which bind optimally to T cells at 4° C., have been reported as common in patients with SLE. However, the in vivo significance of these antibodies is unclear because of the thermal difference between in vitro assays and in vivo pathogenic molecular and cellular mechanisms. Second, warm-reactive IgG anti-T cell antibodies in lupus have been reported. These antibodies have been shown to have heterogeneous specificities against a variety of T cell surface molecules including CD3, CD4, CD45, and IL-2R.

Two distinct roles for these IgM versus IgG anti-T cell antibodies in lupus pathogenesis have been suggested, both of which involve destruction of the cellular targets. IgM is 500-fold more effective in activation of the classical complement pathway, suggesting possible lytic attack of T cells. However, if binding of these cold-reactive IgM molecules only occurs at low temperatures, this would eliminate this possibility in vivo. In addition, the presence of IgM anti-T cell antibodies has not been shown to correlate with lymphopenia in SLE. IgG are less potent complement activators, however their warm-reactivity makes such an in vivo mechanism at least feasible. Other potential roles for anti-T cell IgG have been suggested including antibody dependent cellular cytotoxicity (ADCC) and modulation of T cell signaling and gene expression.

Some reports have suggested that T lymphocyte dysfunction in lupus might be triggered by circulating IgM and IgG anti-T cell autoantibodies rather than due to intrinsic defects although the two possibilities are not mutually exclusive. Collectively, these prior reports have suggested that anti-T cell antibodies are present in some patients with SLE and elucidation of their potential role(s) in disease pathogenesis should consider isotype, thermal amplitude of binding and cytotoxicity, and antigenic specificity.

SUMMARY

In certain aspects, methods and systems are provided for specifically diagnosing or monitoring systemic lupus erythematosus in an individual distinct from a non-systemic lupus erythematosus inflammatory disease or condition, which comprise quantitating, in a blood sample containing white blood cells from the individual, a level of the individual's autoantibodies deposited on or contacting with a surface of a T lymphocyte in the sample.

In certain aspects, kits are provided comprising a) a fluorescently-labeled antibody specifically recognizing an autoantibody which binds to a T lymphocyte, wherein said antibody is an anti-IgG or anti-IgM monoclonal antibody; (b) optionally flouro-conjugated monoclonal antibodies reactive with lineage specific T lymphocyte cell surface markers to distinguish between CD3+CD4+ and CD3+CD8+ T lympocytes; (c) optionally one or more biochemical reagents; and, (d) optionally instructions for use of the kit and the components of (a), (b) and (c) in the diagnosis of systemic lupus erythematosus.

and C4d (T-C4d). 4 distinct groups of SLE patients are indicated, C4d⁻/Ig⁻ (filled circle symbols), C4d⁺/Ig⁺ (filled square symbols), C4d⁺/Ig⁻ (filled triangle symbols), and C4d⁻/Ig⁺ (open circle symbols). (B) T-Ig levels on CD3 T cells from SLE patients (n=326), patients with other diseases (n=185), and healthy controls (n=48) were measured by flow cytometry. The dashed horizontal line indicates the empirically determined cut-off for T-Ig positivity. (C) Levels of C4d and Ig bound on T cells were measured by flow cytometry using a single blood sample obtained on the day of the study visit. Shown are representative results of 10 SLE patients.

Figures 1, 3A:
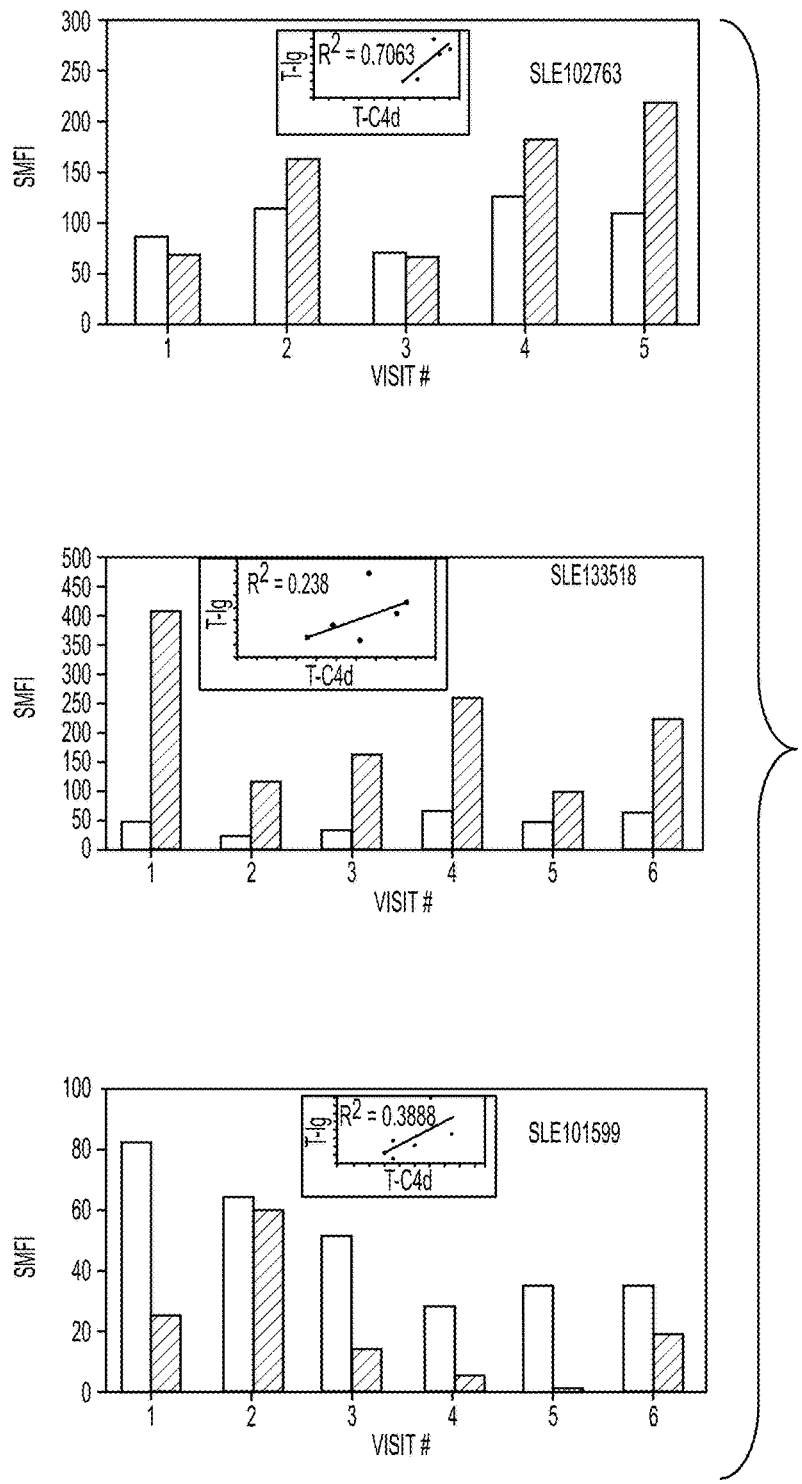
Figures 2, 3A:
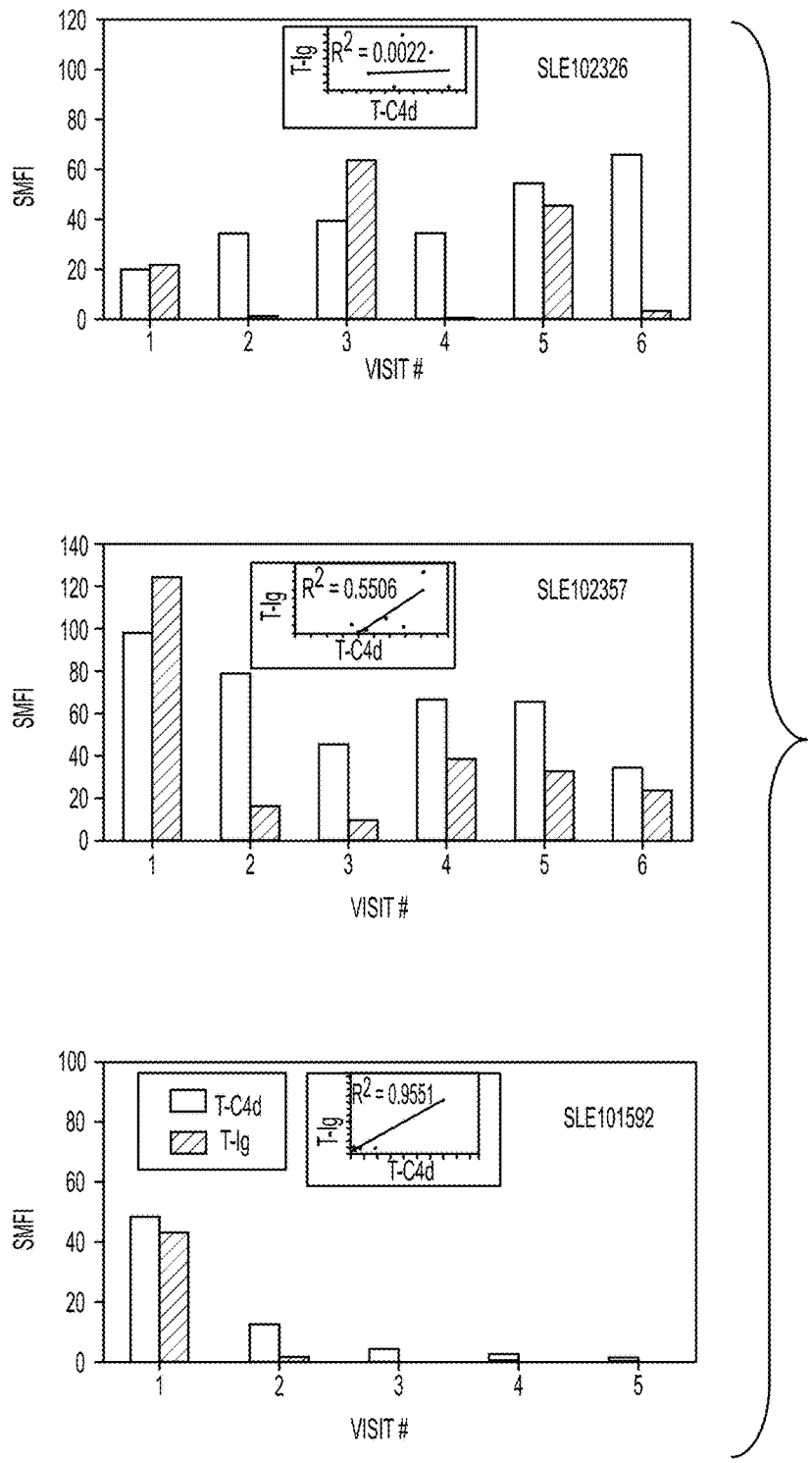
Figure 3B:
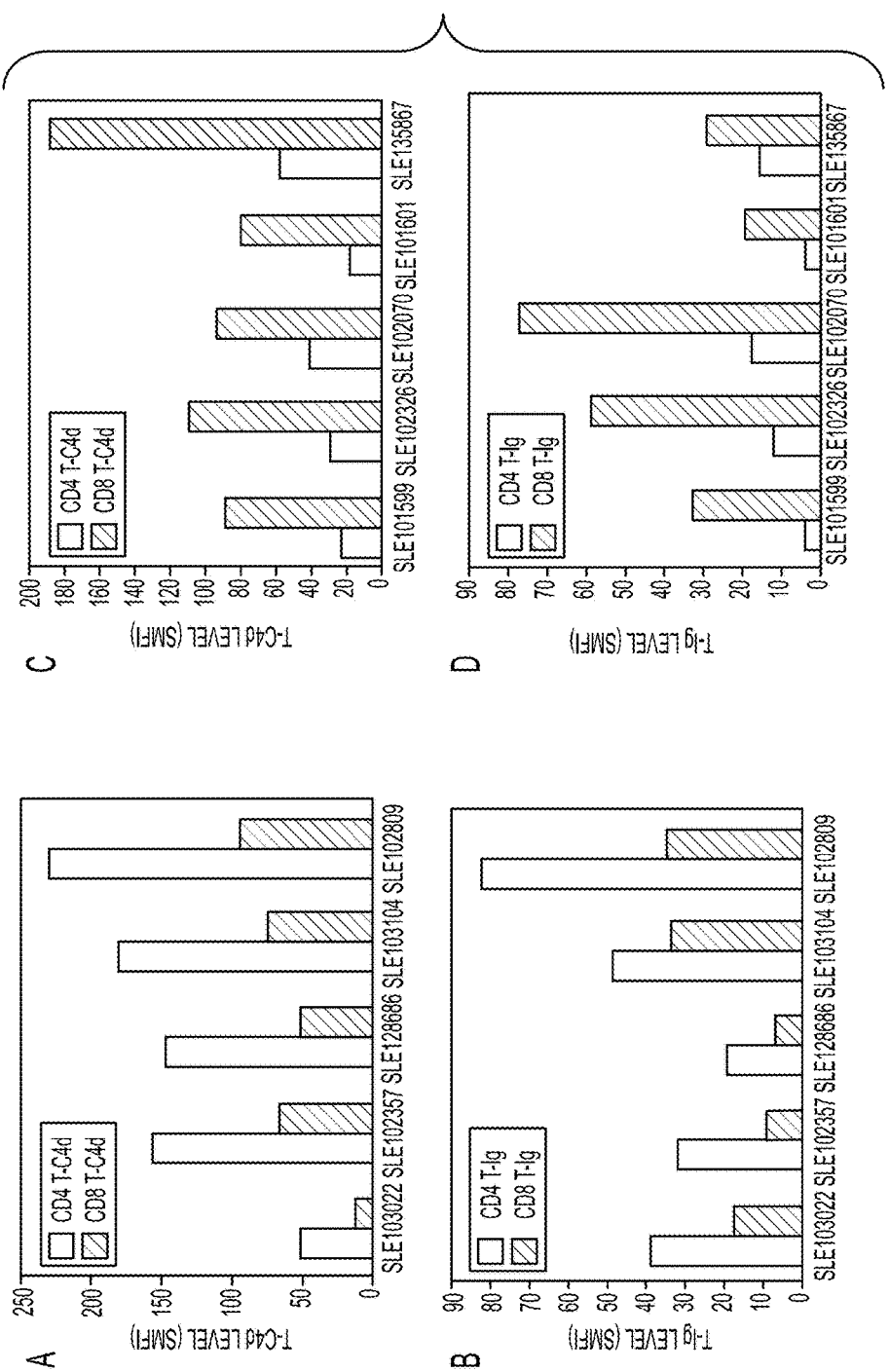

FIGS. 3A-B illustrate that T-C4d and T-Ig levels fluctuate over time, but generally correlate with the levels of specific T cell subsets in SLE patients. (A) Levels of C4d (open columns) and Ig (hatched columns) bound on T cells were measured by flow cytometry using a single blood sample obtained on different study visits. (B) C4d and Ig present on the surface of CD4 (open columns) and CD8 (hatched columns) T cells of SLE patients were measured using multi-color flow cytometric analysis.

Figures 1, 4:
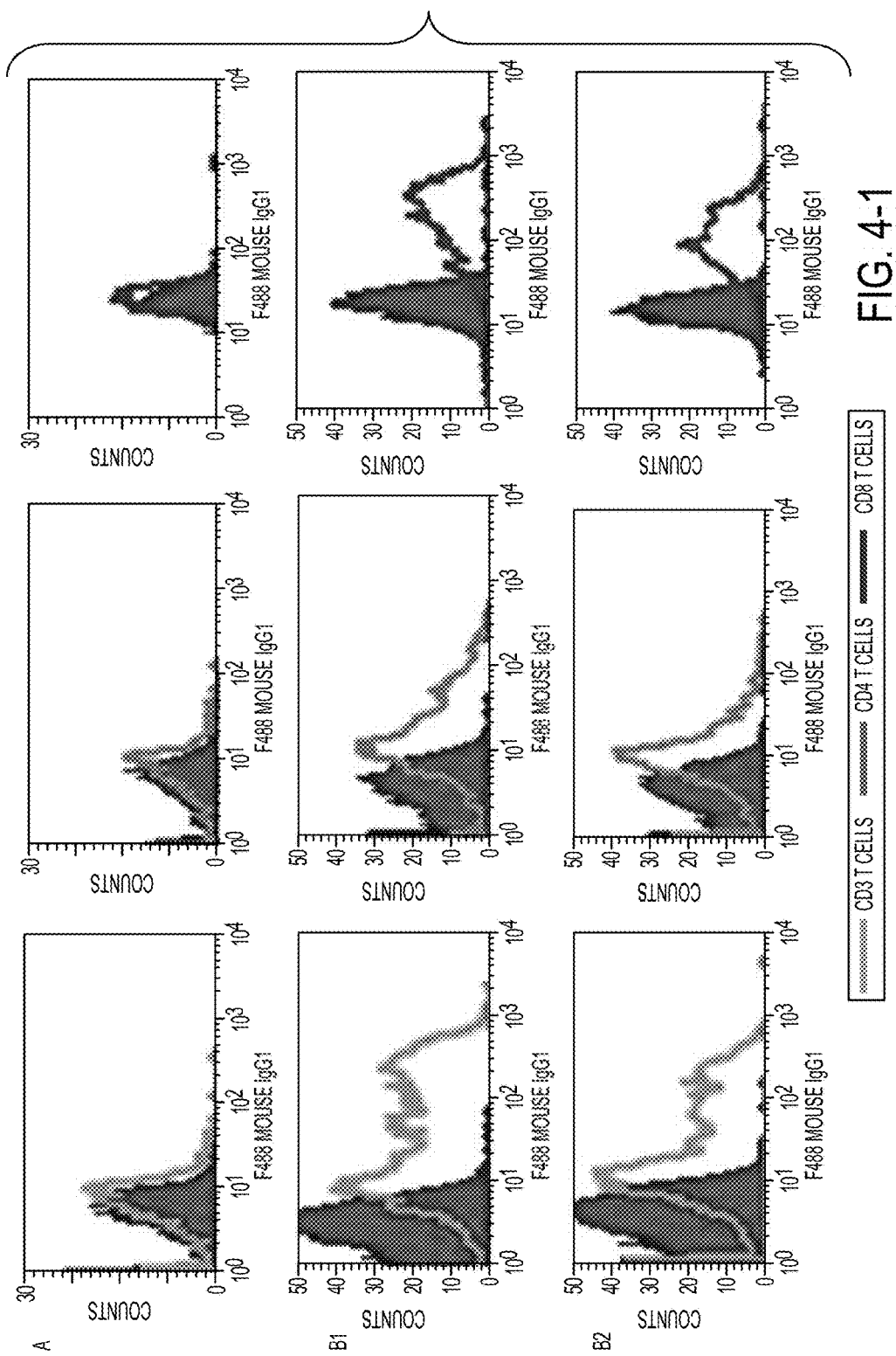
Figures 2, 4:
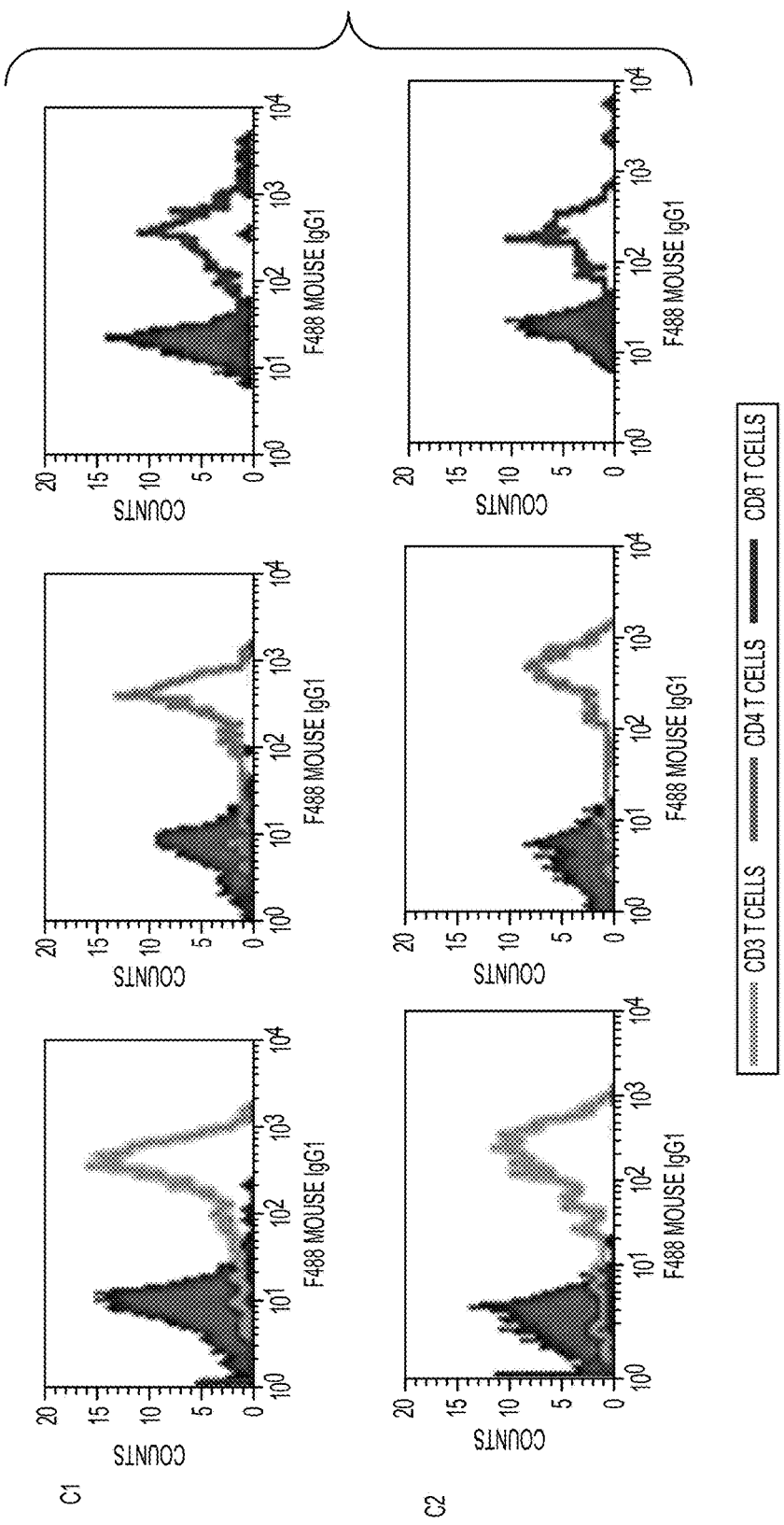
Figures 3, 4:
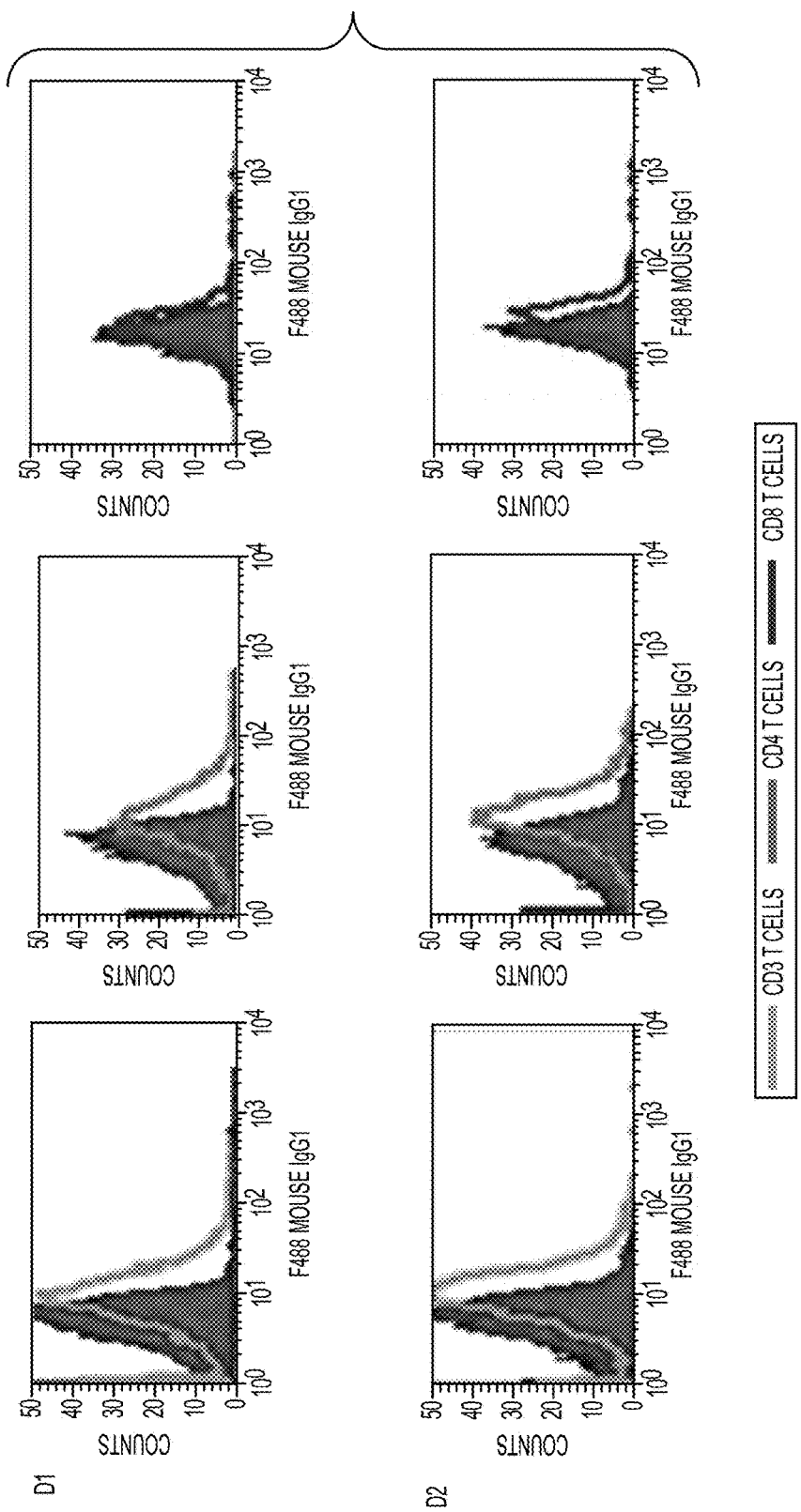

FIG. 4 illustrates that plasma and immunoglobulins transfer the TC4d signature of the donor to normal T cells. PBMC prepared from a healthy control were untreated (panel A; baseline phenotype), or incubated with the plasma (panels B1 and C1) or purified Ig (panels B2 and C2) of two T-C4d+ SLE patients. As a negative control, the cells were incubated with the plasma (panel D1) or purified Ig (panel D2) of a healthy control.

Figure 5B:
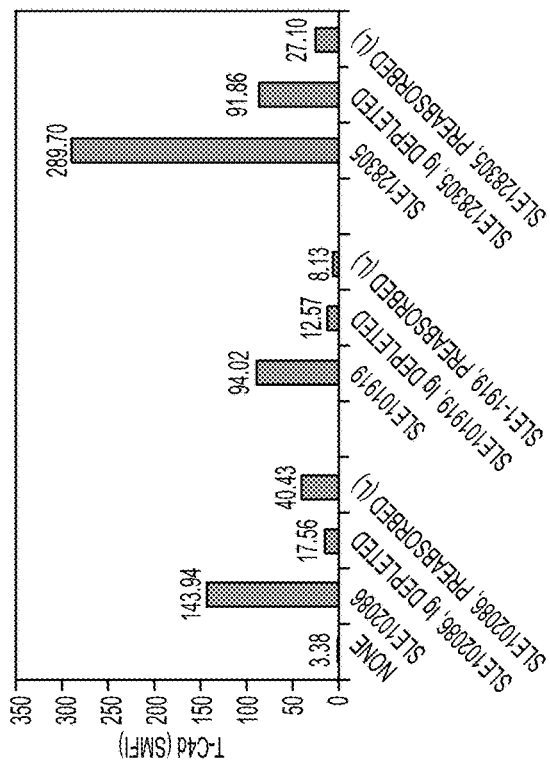
Figure 5A:

FIGS. 5A-B illustrate that anti-T cell autoantibodies from SLE patients can generate T-C4d signatures of the donors on normal T cells. (A) IgG and IgM were purified from the plasma of SLE patients (SLE102086, SLE101606, and SLE102763, with high T-C4d levels), an SLE patient (SLE102771, with low T-C4d level) and healthy controls (HC2009 and HC2034). Purified Ig was used in the in vitro transfer. (B) The plasma of patients SLE102086, SLE101919, and SLE128305 were depleted of IgG and IgM, or pre-absorbed using a large number of leukocytes prepared from a healthy control to deplete lymphocyte-reactive Ig. Ig-depleted or leukocyte-preabsorbed plasma were then used in the in vitro phenotype transfer experiment.

Figure 6A:
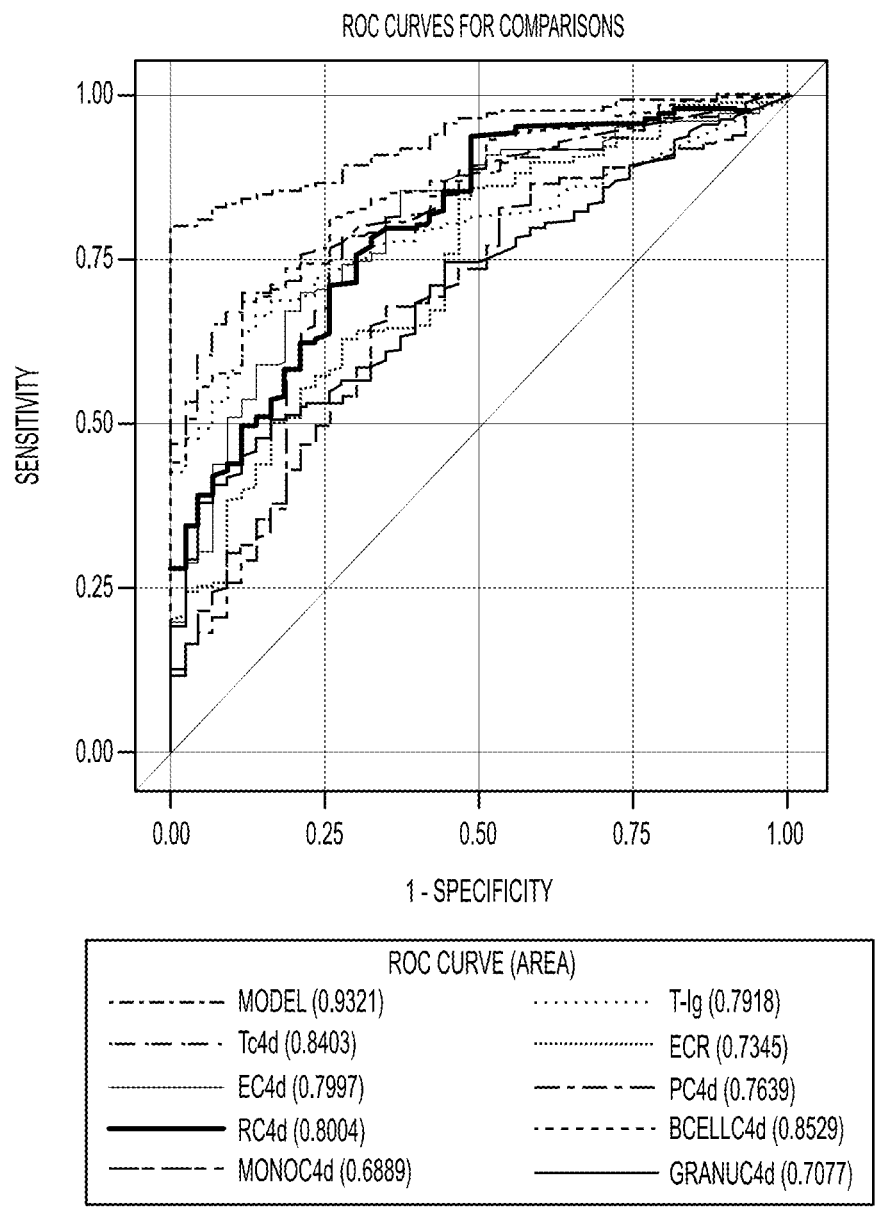
Figure 6B:
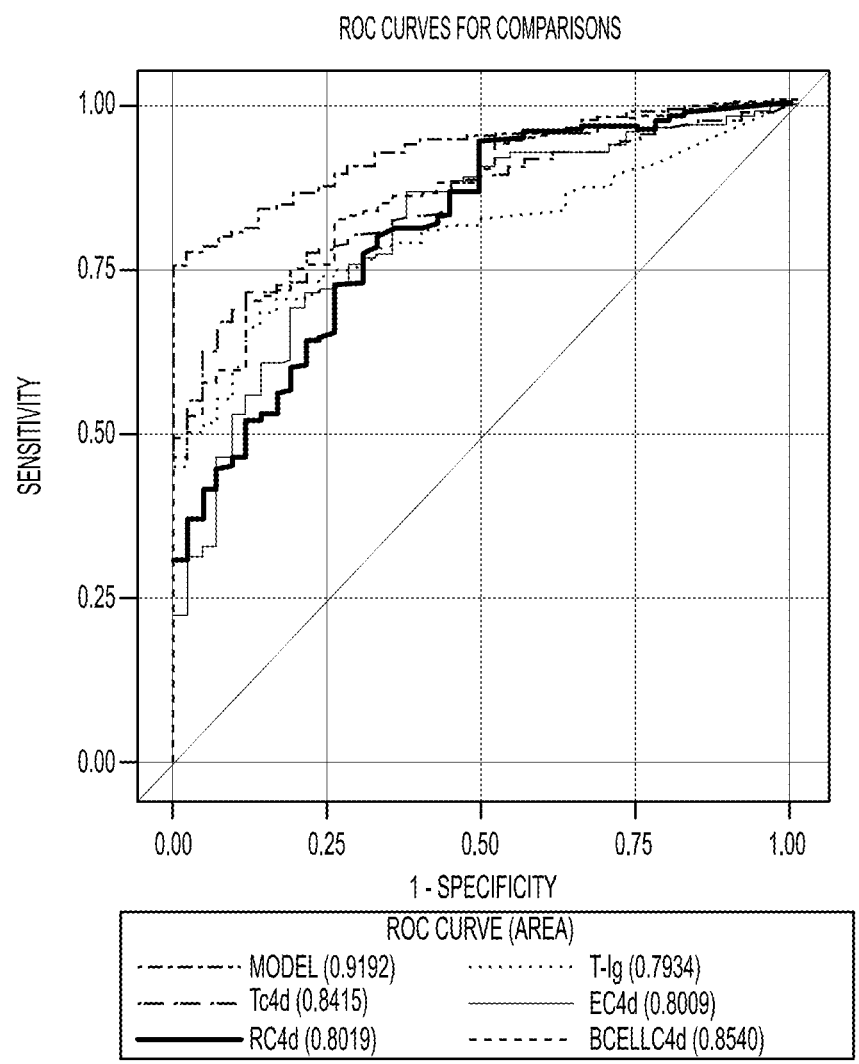

FIGS. 6A-B show ROC comparisons in discriminating SLE and healthy controls. FIG. 6A shows ROC comparisons with all biomarkers measured. FIG. 6B shows ROC comparisons in discriminating SLE and healthy controls with a subset of CB-CAP biomarkers (TC4d, EC4d, RC4d and BC4d).

Figure 7A:
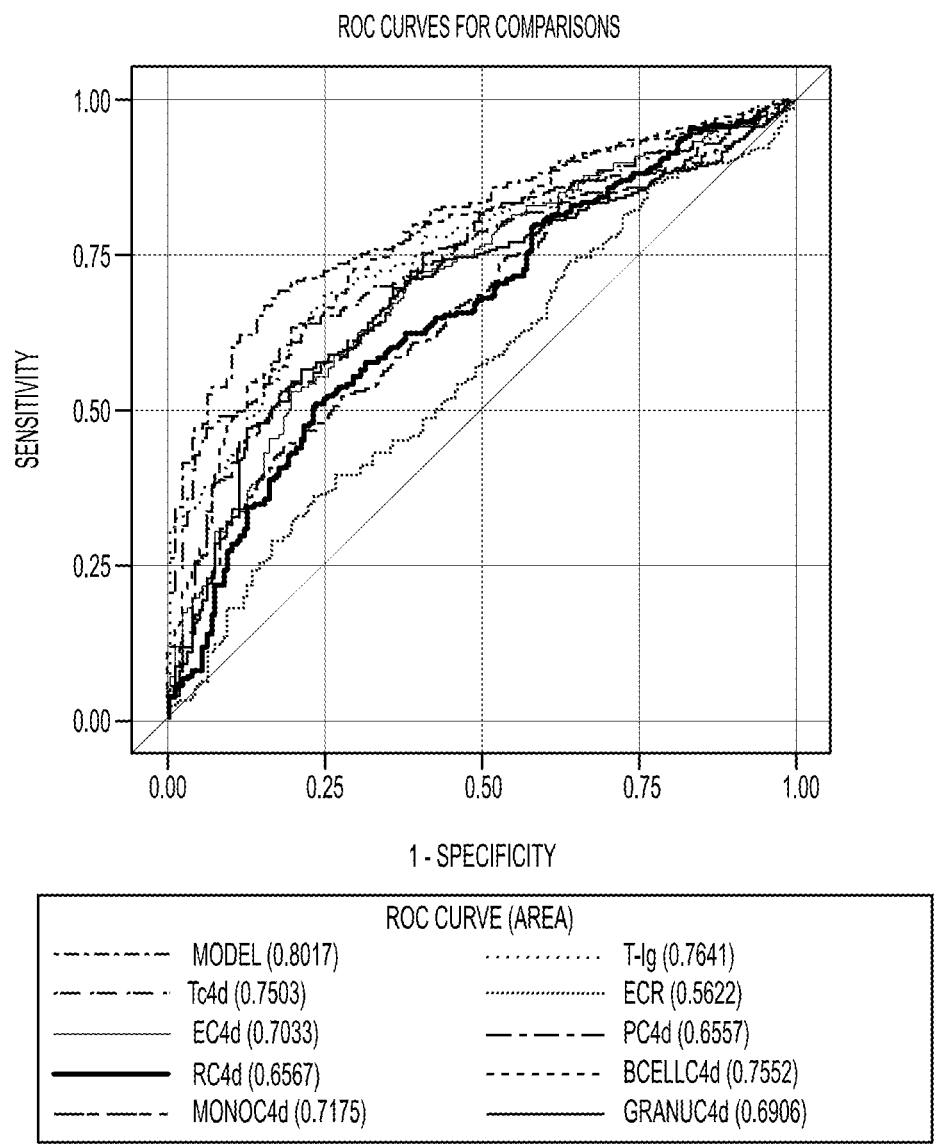
Figure 7B:
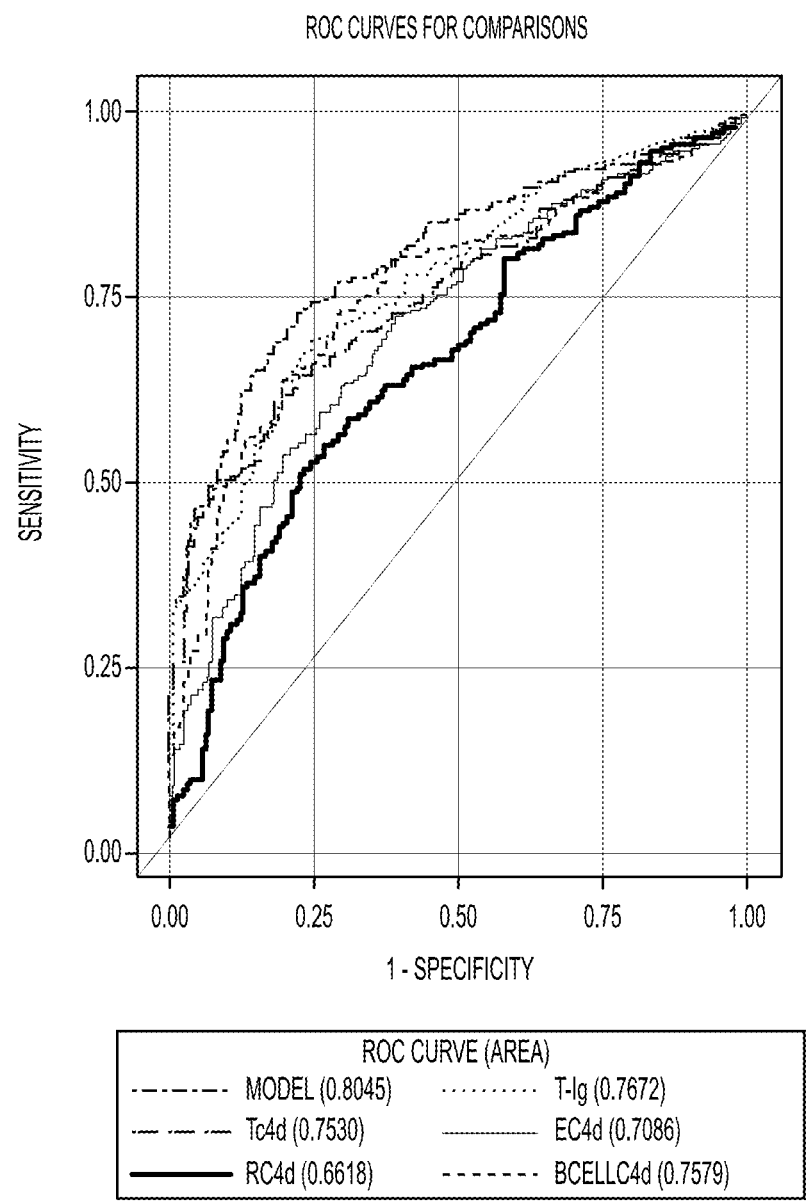

FIGS. 7A-B show ROC comparisons in discriminating SLE and other disease. FIG. 7A shows ROC comparisons with all biomarkers measured. FIG. 7B shows ROC comparisons in discriminating SLE and other disease, with a subset of CB-CAP biomarkers (TC4d, EC4d, RC4d and BC4d).

DETAILED DESCRIPTION

The disclosure of the following patent applications are incorporated herein by reference; (1) Patent Cooperation Treaty Patent Application No. PCT/US13/73983, filed Dec. 10, 2013, titled "Methods and Systems for Using Complement-Tagged Molecules as Biomarkers of Disease;" and (2) Patent Cooperation Treaty Patent Application No. PCT/US14/015032, filed Feb. 6, 2014, titled "Cell-Bound Complement Activation Products as Diagnostic Biomarkers for Pre-Lupus."

As used herein, an "inflammatory disease or condition" refers to any immune disease or condition that causes increased inflammation in an individual. An inflammatory disease or condition also refers to any infectious disease or condition that causes increased inflammation in an individual. In some embodiments the inflammatory disease or condition is a "chronic inflammatory disease or condition." A chronic inflammatory disease or condition is an inflammatory condition that does not resolve after a period of weeks, months or longer. Chronic inflammatory conditions can follow an acute inflammatory condition, or for some diseases or conditions can occur in the absence of an acute inflammatory disease or condition. An inflammatory disease or condition includes the following: SLE, rheumatoid arthritis, vasculitis (and its specific forms such is Wegener's granulomatosis), scleroderma, idiopathic inflammatory myositis, Sjogren's syndrome, serum sickness, transplant rejection, sickle cell anemia, gout, complications of pregnancy such as pre-eclampsia, multiple sclerosis, cardiovascular disease, infectious disease such as hepatitis C virus infection, undifferentiated or overlap connective tissue disease, Raynaud's, osteoarthritis, psoriatic arthritis, primary antiphospholipid syndrome, cutaneous lupus, etc. Each of these diseases or conditions can also be described as chronic inflammatory diseases or conditions.

As used herein, "systemic lupus erythematosus", "SLE", or "lupus" is the prototypic autoimmune disease resulting in multiorgan involvement. This anti-self response is characterized by autoantibodies directed against a variety of nuclear and cytoplasmic cellular components. These autoantibodies bind to their respective antigens, forming immune complexes which circulate and eventually deposit in tissues. This immune complex deposition and consequential activation of the complement system causes chronic inflammation and tissue damage.

As used herein, "non-systemic lupus erythematosus inflammatory disease or condition", "non-SLE inflammatory disease or condition", or "non-lupus inflammatory disease or condition" is any inflammatory disease or condition which is not systemic lupus erythematosus, SLE or lupus, including but not necessarily limited to rheumatoid arthritis, vasculitis (and its specific forms such as Wegener's granulomatosis), scleroderma, idiopathic inflammatory myositis, Sjogren's syndrome, serum sickness, transplant rejection, sickle cell anemia, gout, complications of pregnancy such as pre-eclampsia, multiple sclerosis, cardiovascular disease, infectious disease such as hepatitis C virus infection, undifferentiated or overlap connective tissue disease, Raynaud's, osteoarthritis, psoriatic arthritis, primary antiphospholipid syndrome, cutaneous lupus, etc.

As used herein a "white blood cell" refers to circulating blood cells that are not erythrocytes or reticulocytes, e.g., T and B lymphocytes, NK cells, eosinophils, basophils, granulocytes, neutrophils, monocytes, macrophages, megakaryocytes, plasma cells, circulating endothelial cells, and stem cells.

The peripheral blood mononuclear cell (PBMC) can correspond to any blood cell having a round nucleus. Such cells are known to play a role in the immune response. PBMC include for instance lymphocytes such as T lymphocytes, B lymphocytes and NK cells, monocytes and macrophages.

The PBMC preferably utilized to practice the invention corresponds to a T lymphocyte. The term "T lymphocyte" refers herein to T lymphocytes at any stage of differentiation, including naive CD4⁺ or CD8⁺ T lymphocytes, and mature CD4⁺ or CD8⁺ lymphocytes, such as CD4⁺ Th1 lymphocytes, CD4⁺ Th2 lymphocytes (helper T cells expressing CD4 at their cell surface), and CD8$^+$ cytotoxic cells (cytotoxic T lymphocytes expressing CD8 at their cell surface). To this end, any such subpopulation of cells may be detected through use of an antibody specifically recognizing such a cell-based marker. And more specifically, as an example but not intended as a limitation, the term "antibody specifically recognizing a peripheral blood mononuclear cell (PBMC)" relates to any antibody specifically recognizing such a marker present on a PBMC population, including but not limited to anti-CD3 antibodies if the PBMC population to be detected is the T cell population or anti-CD8 antibodies if the PBMC population to be detected is the cytotoxic T lymphocyte (CTLs) population.

As used herein a "control white blood cell" or a "control PBMC" or a "control T lymphocyte cell" refers to a white blood cell, PBMC or T lymphocyte, as respectively defined herein, that is isolated from an individual who does not have an inflammatory disease or condition, does not have SLE, or shows lower levels of an inflammatory disease or condition (including SLE) whereby comparison with an individual having SLE shows statistically relevant increases in binding or association of autoantibodies to T lymphocytes when compared to any such "control" T lymphocyte. When an inflammatory disease or condition is being diagnosed or monitored in a patient, a control white blood cell, a control PBMC or a control T lymphocyte cell can also refer to a respective cell type isolated from the same patient at an earlier time, e.g., weeks, months, or years earlier.

As used herein a "component of the complement pathway" includes proteins C1, C4, C2, C3 and fragments thereof, e.g., C1q, C1r, C1s, C4a, C4b, C2a, C2b, C4b2a, C3a, C3b, C4c, C4d, iC3b, C3d, C3i, C3dg. Also included are C5, C5b, C6, C7, C8, C9, C1inh, MASP1, MASP2, CR1, DAF, MCP, CD59, C3aR, C5aR, C1qR, CR2, CR3, and CR4, as well as other complement pathway components, receptors and ligands not listed specifically herein.

Certain hardware that may be used to contain or implement various processes and systems in certain embodiments. The hardware may include a processor such as a CPU that operates to execute programming instructions. The programming instructions may be stored on a non-transitory computer readable medium such as read only memory (ROM), random access memory (RAM), a compact disk, a digital disk, flash memory, a memory card, a USB drive, an optical disc storage medium, a distributed computer storage platform such as a cloud-based architecture, and/or other recording medium.

When used in this document, the term "processor" can refer to a single processor or to multiple processors that together implement various steps of a process. Similarly, a "memory device" or "database" can refer to a single device or databases or multiple devices or databases across which programming instructions and/or data are distributed.

Abbreviations
 ALA—anti-lymphocyte autoantibodies
 ADCC—antibody-dependent cellular cytotoxicity
 CB-CAPs—cell-bound complement activation products
 C4d—complement C4 activation product C4d
 Ig—immunoglobulin
 SLE—systemic lupus erythematosus
 T-C4d—T cell-bound C4d T cells bearing C4d, a complement activation product, have been shown to be highly sensitive and specific as diagnostic biomarkers for SLE. T cells bearing C4d are also functionally abnormal, suggesting a role for cell-bound complement activation products (CB-CAPs) in lupus pathogenesis. However, the mechanism responsible for generation of T cells bearing C4d (T-C4d) has not previously been determined. The present inventors have conducted a cross-sectional and prospective study to investigate the potential role of anti-T cell autoantibodies in the generation of the T-C4d signatures in SLE. T cells from patients with SLE, patients with other inflammatory diseases, and healthy controls were characterized for surface deposition of C4d and/or immunoglobulin (Ig) by flow cytometry. Lymphocytes freshly isolated from a patient were directly analyzed for the presence of immunoglobulin (i.e., ALAs) on cell surfaces by flow cytometry, without prior incubation in patient serum or plasma. In vitro phenotype transfer experiments were performed to characterize Ig from SLE patients for the capacity to generate T-C4d signatures in vitro. The results demonstrate that individual patients with SLE harbor specific signatures reflecting the presence of C4d and/or Ig on their T cells and T cell subsets. In addition, SLE patient-specific signatures can be transferred in vitro to normal T cells by exposure to Ig purified from the signature donor. Complement activation does not proceed through generation of C5b-9 (membrane attack complex) or cellular lysis and T-C4d does not correlate with lymphopenia. While not intending to be bound by any theory of operation, these results suggest that patient-specific T-C4d signatures are generated by anti-T cell autoantibodies that trigger sublytic complement activation. This is an important but previously unrecognized link in the complex interplay between autoantibodies and complement activation in lupus pathogenesis. It is believed that a cause and effect relationship between T-Ig and T-C4d whereby T-Ig causes T-C4d deposition may be important not only for lupus diagnosis but also for monitoring disease activity in a lupus patient.

Based on two important characteristics of the deposition of anti-T lymphocyte antibodies and CB-CAPs on the cells, it is believed that the combined assays may be particularly useful for monitoring disease activity in a patient with SLE. First, as the present inventors have demonstrated that anti-T cell antibodies cause deposition of CB-CAPs on the cell surface, detection of anti-T cell antibodies without simultaneous presence of CB-CAPs on the cell surface can be used to predict that CB-CAPs will subsequently be deposited and contribute to increased disease activity. In contrast, the presence of CB-CAPs in the absence of anti-T cell antibodies may indicate that the anti-T cell antibodies were deposited previously and provide insight as to disease activity accordingly. It is believed that simultaneous presence or simultaneously absence of both anti-T cell antibodies and CB-CAPS also can reflect current disease activity or predict future activity. Second, the present inventors have demonstrated previously that CB-CAPS are covalently bound to the surfaces of cells and likely remain permanently bound for the lifespan of the cell once they are deposited. In contrast, anti-T cell antibodies are not covalently bound and therefore may be released from the cell at any time after binding. While not intending to be bound by any theory of operation, it is believed that such a "hit and run" characteristic of the anti-T cell antibodies versus the permanent tagging of a cell by CB-CAPS can provide insight as to when the targeting of the cell(s) occurred and be useful for monitoring and predicting the disease activity of the patient.

One embodiment of the present invention discloses methods for the specific diagnosis and/or monitoring of systemic lupus erythematosus ("SLE") in an individual which is distinct from an individual which may have complications from a different inflammatory disease or condition (i.e., a non-SLE inflammatory disease or condition). Such methodology comprises quantitating the level of the individual's autoantibodies which are deposited upon, contacting, or in some form of stable association with the surface of a T lymphocyte obtained from the individual's blood sample; a sample containing white blood cells, including a population of T lymphocytes. To this end and with regard to the blood sample obtained from an individual for analysis, another embodiment of the present invention discloses methodology wherein the level of the individual's autoantibodies deposited on or contacting with a surface of a T lymphocyte is measured from a population of peripheral blood mononuclear cells obtained from the individual's blood sample.

It will be understood upon review of this specification that any representative T lymphocyte cell type is covered by the scope of this disclosed methodology, namely T lymphocytes obtained from an individual's blood sample which may be a T lymphocyte represented and therefore selected from the group consisting of a CD4+ Th1 lymphocyte cell, a CD4+ Th2 lymphocyte cell, a CD8+ cytotoxic lymphocyte cell, as well as other CD4+ lymphocyte cells, including but not limited to CD4+ Th9 helper cells, CD4+ Th17 helper cells, CD4+ T follicular helper (Tfh) cells, and CD4+ regulatory T (Treg) cells.

While these embodiments relate to a single and focused detection and quantitation of anti-T cell autoantibodies present within the individual as a specific determiner of SLE as opposed to a non-SLE inflammatory disease or condition, a further embodiment of the invention comprises the focus of quantitating, in addition the quantitation of these anti-T cell autoantibodies present within the individual, detecting and quantifying the level of a diagnostic biomarker of SLE also deposited on or contacting with a surface of the T lymphocyte cell obtained from a blood sample (such as PBMCs), wherein this secondary diagnostic biomarker is selected from the group consisting of C4d, C3d, a C4 component of the complement pathway and a C3 component of the complement pathway. In embodiments, a preferred secondary diagnostic biomarker is C4d.

Another embodiment discloses methods for the specific diagnosis and/or monitoring of SLE in an individual which is distinct from an individual which may have complications from a different inflammatory disease or condition (i.e., a non-SLE inflammatory disease or condition) wherein one step comprises quantitating the level of the individual's autoantibodies which are deposited upon, contacting, or in some form of stable association with a surface of a T lymphocyte obtained from the individual's blood sample which contain a population of white blood cells, (including but not limited to a preparation of PBMCs isolated from the individual); and combined with an additional step which involves obtaining a similar 'control' sample (as defined herein and containing a population of T lymphocytes, such as prepared from a population of peripheral blood mononuclear cells obtained from the control blood sample) and comparing the level from the tested individual against the level of autoantibodies deposited on or contacting with a surface of a control population of T lymphocytes, wherein an increased level of autoantibodies from the sample in the tested individual identifies SLE within that individual. Again, it will be understood that this particular embodiment intends as a representative T lymphocyte cell type any such T lymphocyte which may be obtained from an individual's blood sample selected from the group consisting of a CD4+ Th1 lymphocyte cell, a CD4+ Th2 lymphocyte cell, a CD8+ cytotoxic lymphocyte cell, as well as other CD4+ lymphocyte cells, including but not limited to CD4+ Th9 helper cells, CD4+ Th17 helper cells, CD4+ T follicular helper (Tfh) cells, and CD4+ regulatory T (Treg) cells.

Additionally, it is contemplated, and disclosed herein, that measurement of both a test (i.e., individual's) sample containing the population of T lymphocytes and a 'control' sample containing a population of control T lymphocytes may further encompass, as disclosed above, the additional measurement quantitating the level of an additional or set of additional diagnostic biomarkers associated with SLE which also are known to deposit or contact the surface of a T lymphocyte, wherein such a diagnostic biomarker is selected from the group consisting of C4d, C3d, a C4 component of the complement pathway and a C3 component of the complement pathway. In embodiments, a preferred biomarker is C4d.

Another embodiment as disclosed herein covers a method of specifically diagnosing or monitoring SLE in an individual distinct from a non-SLE inflammatory disease or condition, which comprises the steps of obtaining a blood sample containing white blood cells from the individual, isolating a peripheral blood mononuclear cell population from the blood sample, incubating the peripheral blood mononuclear cell population with a detectable reagent which specifically binds to an autoantibody bound to the cell surface of a T lymphocyte within the peripheral blood mononuclear cell population, forming a T lymphocyte-autoantibody-detectable reagent complex, and measuring the level of the T lymphocyte-autoantibody-detectable reagent complex. This methodology is well suited to measuring, recognizing or quantitating such as T lymphocyte-autoantibody-detectable reagent complex through any known methodology described in the art related to flow cytometry. As disclosed above with regard to comparing the level of any such complex from a test individual as compared to a control sample, this embodiment also contemplates comparing the level of the T cell-autoantibody-detectable reagent complex obtained from the individual with a level of a like T lymphocyte-autoantibody-detectable reagent complex obtained from a control blood sample. Such a measurement comparison between a test and control sample will be additionally informative in diagnosing or continually monitoring SLE within a particular individual.

It is further disclosed herein that a detectable reagent may be a fluorescently-labeled anti-human Ig antibody which is detectable by flow cytometry, and in particular, as disclosed throughout this specification, may include, but in no way be limited to, a fluorescently-labeled anti-human Ig antibody selected from the group consisting of a fluorescently-labeled anti human IgG antibody and a fluorescently-labeled anti-human IgM antibody.

Another embodiment provides a kit for the specific diagnoses or monitoring of SLE in an individual. The kit can include a fluorescently-labeled antibody specifically recognizing an autoantibody which binds to a T lymphocyte (including but in no way limited to an anti-IgG or anti-IgM monoclonal antibody), optionally including a flouro-conjugated monoclonal antibodies reactive with lineage specific T lymphocyte cell surface markers to distinguish between CD3+ CD4+ and CD3+ CD8+ T lymphocytes, optionally including one or more biochemical reagents; and, optionally including instructions for use of the kit and the kit components in the diagnosis or monitoring of SLE. Any such kit may also be suitable for, as disclosed herein, the identification of one or additional biomarkers (beyond the individual's autoantibodies found to bind T lymphocytes), which may include but are in no way limited to the inclusion within the kit of flouro-conjugated monoclonal antibodies reactive to a specific T lymphocyte cell surface marker selected from the group consisting of CD3, CD4, CD8, CXCR3, CCR4, Crth2, CCR6, CXCR5 and CD25.

The determinations used for specifically diagnosing or monitoring SLE in an individual distinct from a non-SLE inflammatory disease or condition through measurement of at least T cell-autoantibody-detectable reagent complex, and possibly the additional measurement of complement pathway components (including but not limited to C4d and/or C3d), and in conjunction with the diagnostic and disease activity monitoring methods described above can be carried out manually, but often are conveniently carried out using an automated system and/or equipment, in which the blood sample (or e.g., the isolated PBMC fraction) is analyzed automatically to make the necessary determination or determinations, and the comparison with the base or reference value is carried out automatically, using computer software appropriate to that purpose.

Thus, one embodiment of the invention comprises a computer-based system for specifically diagnosing or monitoring systemic lupus erythematosus in an individual distinct from a non-systemic lupus erythematosus inflammatory disease or condition, the system comprising a processor and a non-transitory computer-readable storage medium containing programming instructions configured to, when executed, instruct the processor to quantitate, in a blood sample containing white blood cells from the individual, a level of the individual's autoantibodies deposited on or contacting with a surface of a T lymphocyte in the sample, and to then compare the individual's level with a level of autoantibodies deposited on or contacting with a surface of a control T lymphocyte, wherein an increased level of autoantibodies from the sample from the individual identifies SLE in the individual. To this end, any such computer software, or computer-readable media for use in the methods of this invention may include a computer readable medium comprising code for receiving data corresponding to the level of the individual's autoantibodies deposited on or contacting with a surface of a T lymphocyte is measured from a population of peripheral blood mononuclear cells obtained from the blood sample, wherein the T lymphocyte is represented in the sample by at least one T lymphocyte cell type including, but not limited to, a representative T lymphocyte selected from the group consisting of a CD4+ Th1 lymphocyte cell, a CD4+ Th2 lymphocyte cell, a CD8+ cytotoxic lymphocyte cell, as well as other CD4+ lymphocyte cells, including but not limited to CD4+ Th9 helper cells, CD4+ Th17 helper cells, CD4+ T follicular helper (Tfh) cells, and CD4+ regulatory T (Treg) cells. Additionally, any such computer software, or computer-readable media for use in the methods of this invention may include a computer readable medium comprising code for receiving data corresponding to the level of an additional biomarker associated with SLE which also are known to deposit or contact the surface of a T lymphocyte, wherein the diagnostic biomarker is selected from the group consisting of C4d, C3d, a C4 component of the complement pathway and a C3 component of the complement pathway, with a single preference being C4d. Another aspect concerns such computer software, or computer-readable media for use in the methods of this invention to include a computer readable medium comprising code for receiving data corresponding to the level of the individual's use of any additional kit component, such as flouro-conjugated monoclonal antibodies reactive to a specific T lymphocyte cell surface marker selected from the group consisting of CD3, CD4, CD8, CXCR3, CCR4, Crth2, CCR6, CXCR5 and CD25, as described herein.

The present inventors have previously demonstrated that complement activation products, particularly C4d, bind at high levels specifically to circulating cells in patients with SLE, thereby generating CB-CAP signatures that are highly sensitive and specific for a lupus diagnosis. The majority of patients with lupus harbor erythrocytes, lymphocytes, platelets and other circulating cells bearing C4d and/or C3d in cell-specific patterns that are unique to individual patients. The mechanism(s) responsible for generating these CB-CAP signatures have not been previously identified. The present inventors hypothesized that anti-cell specific autoantibodies may be responsible for CB-CAP deposition and focused specifically on the potential role of anti-T cell autoantibodies. Evidence is provided herein to support the role of anti-T cell autoantibodies in the generation of TCD3-C4d, TCD4-C4d and TCD8-C4d signatures through sublytic complement activation and suggest that this is a previously unrecognized pathogenic mechanism in lupus.

First, it has been demonstrated previously that more than 80% of patients with lupus bear CB-CAP signatures, which are highly patient-specific. The mechanism(s) responsible for these signatures has not been previously determined. Autoantibodies would be natural suspects for generation of specific patterns of C4d deposition on cell surfaces, however antibody-mediated activation of complement on cell surfaces is generally thought to result in destruction of the cell as observed in hemolytic anemia and in monoclonal antibody-mediated B cell depletion therapies with agents such as rituximab. The present inventors have demonstrated herein that anti-T cell autoantibodies are present on circulating T cells in lupus patients, and T-Ig/T-C4d patterns are consistent among individual patients over time. Furthermore, IgM and IgG purified from lupus patients bearing Ig and C4d on their T cells can transfer the T-C4d signature to healthy T cells. Collectively, these observations support that activation of the classical complement pathway on surfaces of T cells commonly occurs in patients with SLE. The lack of correlation between T-C4d signatures and lymphopenia and the lack of membrane attack complex on these T cells demonstrate that activation of the classical pathway does not proceed through significant generation of C5 convertases.

Second, anti-T cell autoantibodies in patients with SLE were first discovered more than 40 years ago yet no clear role in disease pathogenesis has been defined. One challenge has been to reconcile how cold-reactive IgM might be pathogenic at in vivo thermal conditions. While not intending to be bound by any theory of operation, it is suggested from the studies described herein that low concentrations of IgM autoantibodies are capable of binding to T cells in vivo leading to deposition of C4d without causing cell lysis.

Third, the results of the present study may explain a curious observation described in all reports of CB-CAPS to date. Specific cell types bearing abnormal levels of C4d are almost always uniformly positive in a given patient, as reflected by the flow cytometric histograms. For example, if the CB-CAP signature of a patient includes TCD3-C4d, all CD3 cells in that patient will be C4d-positive and the levels of C4d on each cell will be similar. This is in contrast to patterns generated by circulating immune complex deposition on cells, which might bind to only a subset of cells bearing receptors for Fc or complement activation products. While not intending to be bound by any theory of operation, it is believed that circulating anti-T cell autoantibodies in patients with lupus have the capacity to recognize all circulating T lymphocytes and thereby generate C4d deposition on each cell. This model explains the homogeneous CB-CAP patterns observed on T cells and possibly other cells.

Fourth, while not intending to be bound by any theory of operation, the observations described herein further support the hypothesis that CB-CAP signatures are not generated by systemic complement activation and deposition on innocent bystander cells but rather through a cell-specific targeting mechanism.

While not intending to be bound by any theory of operation, T-Ig single-positive patients might be explained by Ig binding to target T cells in a reversible manner during disease flares, catalyzing deposition of C4d on the T cells. C4d, once generated and bound covalently to T cell surfaces, may remain stable even when the initiating autoantibodies have detached from T cells. Anti-T cell autoantibodies of certain IgG subclasses (e.g., IgG2 and IgG4) may be inefficient in triggering activation of the complement system, thereby creating a phenotype of binding of Ig without C4d. The presence of additional ALA-independent mechanisms whereby CAPs are generated and deposited on T cells is possible. However, in view of the characteristic autoantibody overproduction in patients with SLE, it it believed that the ALA-mediated mechanism is likely to play a dominant role in cultivating the cell- and patient-specific T-C4d phenotypes.

The present inventors have shown that deposition of C4d on T cells and T cell subsets is generated by sublytic complement activation triggered by anti-T cell autoantibodies in patients with SLE. While not intending to be bound by any theory of operation, this previously unrecognized pathway might be a vicious pathogenic circle whereby autoantibodies activate the classical complement pathway in a sublytic capacity. Deposition of C4d contributes to the dysfunction of these targeted cells, which remain in the circulation and drive further immune dysregulation, autoantibody production, complement activation and tissue damage.

The following examples serve to further illustrate the present invention.

EXAMPLES

Example 1

Materials and Methods

Study Participants

SLE Patients

Three hundred and twenty-six patients who met the American College of Rheumatology classification criteria for definite SLE were initially recruited and followed.

Patients with Other Diseases

A total of 185 patients with various non-SLE autoimmune diseases such as rheumatoid arthritis, Sjögren's syndrome, scleroderma, idiopathic inflammatory myopathy, primary anti-phospholipid syndrome, and undifferentiated connective tissue disease were recruited during the same time period as were the SLE patient cohort.

Healthy Controls

A total of 48 healthy individuals were recruited through local advertisements. To confirm their healthy status, participants completed a brief questionnaire regarding existing medical conditions.

Plasma and Serum Preparation, Immunoglobulin Isolation, and Immunoglobulin Depletion At the time of each participant's visit, a 4.5-ml sample of blood was collected into a Vacutainer® tube containing EDTA as an anticoagulant (Becton Dickinson, Franklin Lakes, N.J.). EDTA-anticoagulated blood samples were processed within 24 hours after blood drawn. Plasma was fractionated by centrifugation at 800×g for 10 minutes and stored at 4° C. (for immediate, short-term use) or −80° C. (for future, long-term use). Normal human serum was prepared from the blood of a healthy control collected into a serum separation tube without anticoagulant, aliquoted, and stored at −80° C. until use. Immunoglobulin G (IgG) present in the plasma was isolated using Pierce ImmunoPure® (A/G) IgG purification kit (Thermo Scientific, Rockford, Ill.) following the manufacturer's instruction. After collection of IgG, the flow-through from the protein A/G affinity column was further fractionated to enrich for IgM using the Pierce Nab™ Protein L Spin purification kit (Thermo Scientific) following the manufacturer's instruction. The IgG and IgM fractions eluted from the respective affinity column were desalted, buffer-changed into phosphate-buffered saline (PBS), and concentrated by centrifugation using Microcon® centrifugal filters (molecular weight cutoff 30 kD; EMD Millipore, Billerica, Mass.). To deplete Ig, the plasma sample was passed through sequentially the protein A/G column and protein L column twice. The final flow-through was collected, dialyzed against PBS, and concentrated back to the original volume using the Microcon® device. To deplete lymphocyte-reactive Ig, the plasma sample (50 µl) was incubated with peripheral blood lymphocytes ($10^7$ cells; isolated from individual healthy controls) at 4° C. for 30 minutes and then recovered by removal of cells by centrifugation.

Isolation of Peripheral Blood Mononuclear Cells

Peripheral blood mononuclear cells (PBMC) were isolated from EDTA-anticoagulated blood samples within 24 hours after blood drawn by gradient centrifugation. Briefly, blood samples were centrifuged to separate the plasma and cells. The cell fraction was diluted with 3 volumes of PBS, layered on top of Ficoll-Paque™ Plus solution (GE Healthcare Bio-Sciences, Piscataway, N.J.), and centrifuged at 400×g at room temperature for 20 minutes. Mononuclear cells located at the interface between the plasma and Ficoll solution were carefully transferred into a fresh tube, washed extensively with PBS to remove contaminating platelets, and resuspended in PBS.

Flow Cytometric Assays for T Cell-Bound C4d (T-C4d) and T Cell-Bound Immunoglobulin (T-Ig) Measurement PBMC prepared from EDTA-anticoagulated blood were divided into equal-volume aliquots for CB-CAP detection. Levels of C4d and Ig bound to T cells were measured using a multicolor flow cytometric assay recently developed, with some modifications. Lymphocytes, monocytes, and residual granulocytes were distinguished based on the expression of characteristic surface molecules and their unique features of forward (size)/side (granularity) scattering. Phycoerythrin (PE)-, PE-Cy5-, or allophycocyanin (APC)-conjugated mouse monoclonal antibodies (mAb) reactive with lineage-specific cell surface markers (CD3, CD4, and CD8 for T cells; BD Biosciences, San Diego, Calif.) were used in conjunction with either mouse monoclonal anti-human C4d mAb (mouse IgG1; reactive with C4d-containing fragments of C4; Quidel, San Diego, Calif.), anti-human IgG (mouse IgG1; BD Biosciences), or anti-human IgM (mouse IgG1; BD Biosciences) that had been labeled with Alexa Fluor dyes using the Zenon antibody labeling kit (Life Technologies, Carisbad, Calif.). Alternatively, PE-conjugated anti-human Ig kappa chain or PE-conjugated anti-human Ig lambda chain (BD Biosciences) was used in combination with anti-C4d and anti-cell surface marker antibodies to identify the light chain subtypes of T cell-bound Ig. After staining, cells were analyzed using a FACSCalibur™ flow cytometer and CELLQuest software (Becton Dickinson Immunocytometry Systems). To ensure the specificity of the antibody staining detected, leukocyte aliquots from each patient stained with mouse IgG of appropriate isotypes were routinely included in all experiments. To ensure the day-to-day reliability of LB-CAP measurements, the FACSCalibur flow cytometer was calibrated daily using CaliBrite 3 beads and FACSComp software (Becton Dickinson Immunocytometry Systems). Levels of cell-bound C4d and Ig were expressed as specific median fluorescence intensity (SMFI), which was calculated as the C4d (or Ig)-specific median fluorescence intensity minus the isotype control median fluorescence intensity.

In Vitro Phenotype Transfer Experiments

PBMC ($10^6$ cells in 50 µl of PBS), isolated from individual healthy controls or SLE patients with low T-C4d levels, were incubated with 50 µl of the plasma prepared from individual SLE patients who had been identified as having the high T-C4d/T-Ig phenotype based on the flow cytometric analysis described above. In some experiments, the SLE plasma was replaced with different amounts of purified IgG or IgM (100-1000 µg), Ig-depleted plasma, or lymphocyte-preabsorbed plasma. After incubation at 4° C. for 30 min, the PBMC suspension was washed with PBS twice, resuspended in 50 µl of $GVB^{2+}$ buffer (1% gelatin, 5 mM Na veronal, 142 mM NaCl, pH 7.3), and incubated with 50 µl of normal human serum (as a source of complement). In some cases, heat-inactivated normal human serum or C1q-depleted human serum (Quidel) was used as a negative control serum. After incubation at 37° C. for 40 minutes, the cell suspension was washed with PBS twice and subjected to multi-color flow cytometric assay described above.

Example 2

Figure 1:
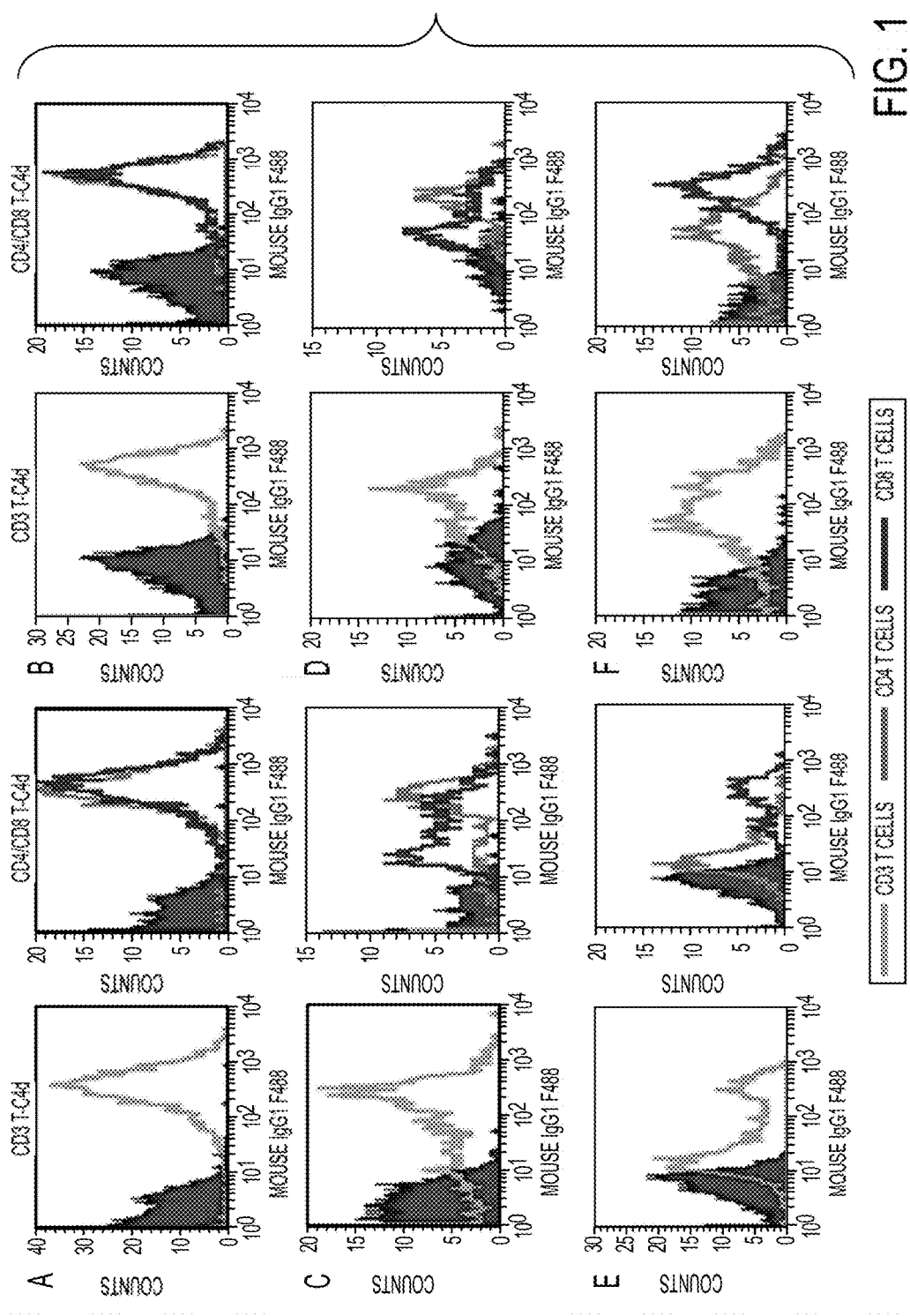
FIG. 1 illustrates that C4d can bind differentially to CD4 versus CD8 T cells in SLE patients. Levels of C4d bound to T cells bearing CD3, CD4 or CD8 were measured simultaneously using a single blood sample obtained on the day of the study visit. Flow cytometric histograms from 6 representative SLE patients are shown to illustrate the presence of similar (panels A and B) or distinct (panels C-F) levels of C4d on CD4 T and CD8 T cells in the same patient at a given time. Closed histograms represent Ig isotype control staining; open histograms represent C4d-specific staining

TCD3-C4d, TCD4-C4d and TCD8-C4d Patient-Specific Signatures are Generated in SLE A cross-sectional study was conducted to identify patients in whom levels of C4d on T cells were either similar or distinct between CD4 and CD8 subsets. In some patients the C4d-staining histogram of CD3+ T (TCD3) cells reflected a single population of cells and the C4d-staining histograms of CD4+ T (TCD4) cells and CD8+ T (TCD8) cells were indistinguishable, reflecting equal levels of C4d binding to each of the two cell subsets (FIG. 1, panels A and B). However, biphasic TCD3-C4d histograms were observed in many of the SLE patients (FIG. 1, panels C-F). TCD4-C4d and TCD8-C4d assays demonstrated that these biphasic histograms were due to differences in the levels of C4d on these two cell subsets within individual patients. In some patients, considerably elevated levels of C4d were detected on TCD4 cells, compared to TCD8 cells (FIG. 1, panels C and D). Conversely, significantly higher levels of C4d could be present on TCD8 cells compared to TCD4 cells in other patients (FIG. 1, panels E and F). In general, the TCD4-C4d/TCD8-C4d-specific preferential binding profile, or signature, of a given patient appeared to remain stable over time, although the actual levels of C4d present on the cells might fluctuate over time (Table 1). There were exceptions to this pattern. A "conversion" of the binding pattern did occur in some patients during their disease course (e.g., patients SLE56525 and SLE102357, Table 1). As previously reported, complement C5b-9 (membrane attack complex) was not detected on the T cells. While not intending to be bound by any theory of operation, this observation that T cell subsets could be preferentially targeted by C4d deposition and patient-specific T-C4d signatures could be identified suggested that specific mechanisms might be responsible for generating these phenotypes. T-C4d signatures were not associated with lymphopenia (not shown).

TABLE 1

Differential Binding of C4d to T Cell Subsets in SLE Patients Over Time

| Patient ID | Study Date | CD3 T-C4d (SMFI) | CD4 T-C4d (SMFI) | CD8 T-C4d (SMFI) |
|---|---|---|---|---|
| SLE103343 | Mar. 5, 2009 | 309.44 | 324.16 | 320.31 |
| SLE103343 | Dec. 1, 2009 | 417.70 | 407.33 | 422.02 |
| SLE103343 | Nov. 4, 2011 | 1052.43 | 911.22 | 1086.94 |
| SLE107395 | May 4, 2012 | 404.24 | 376.10 | 411.57 |
| SLE107395 | May 26, 2012 | 627.99 | 693.17 | 602.55 |
| SLE107395 | Feb. 1, 2013 | 228.43 | 302.68 | 236.17 |
| SLE8383 | May 18, 2005 | 7.55 | 3.92 | 231.71 |
| SLE8383 | Jan. 4, 2006 | 13.91 | 8.17 | 258.09 |
| SLE8383 | Sep. 25, 2007 | 10.85 | 6.29 | 152.80 |
| SLE101601 | Sep. 1, 2009 | 57.58 | 38.76 | 108.67 |
| SLE101601 | Mar. 6, 2012 | 184.38 | 99.19 | 250.36 |
| SLE101601 | Dec. 6, 2012 | 126.39 | 74.33 | 250.74 |
| SLE56525 | Apr. 3, 2008 | 35.63 | 24.54 | 95.08 |
| SLE56525 | Oct. 10, 2011 | 177.10 | 133.54 | 451.16 |
| SLE56525* | Jan. 24, 2012 | 322.26 | 259.39 | 169.35 |
| SLE102763 | Jan. 17, 2008 | 67.04 | 155.94 | 30.95 |
| SLE102763 | Jul. 1, 2008 | 182.99 | 213.69 | 125.35 |
| SLE102763 | Oct. 16, 2008 | 220.42 | 241.32 | 129.61 |
| SLE102683 | Dec. 14, 2010 | 137.34 | 192.43 | 66.04 |
| SLE102683 | Jun. 16, 2011 | 58.20 | 130.87 | 31.99 |
| SLE102683 | Dec. 6, 2011 | 129.57 | 234.16 | 34.54 |
| SLE102357 | Apr. 14, 2011 | 82.37 | 133.38 | 39.60 |
| SLE102357 | Dec. 1, 2011 | 170.33 | 191.28 | 44.54 |
| SLE102357* | Apr. 19, 2012 | 80.57 | 68.99 | 147.62 |
| SLE102357 | Jan. 29, 2013 | 51.56 | 42.10 | 94.00 |

Example 3

Immunoglobulin and C4d are Simultaneously Present on T Cells in SLE

Figure 2A:
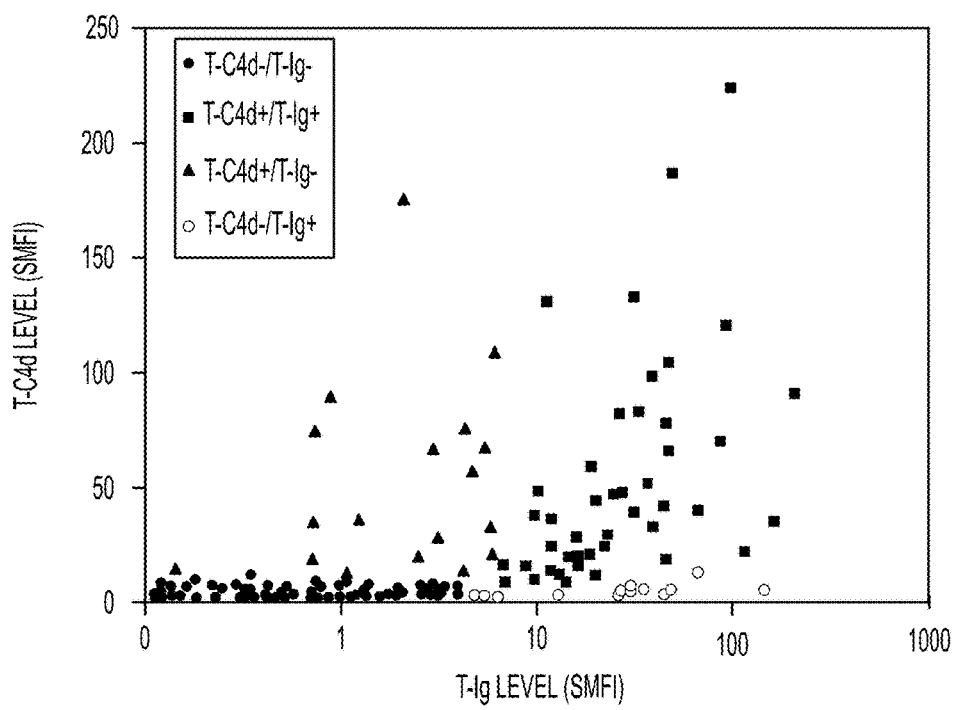
FIGS. 2A-C illustrate that C4d and Ig are simultaneously present on the surface of T cells in SLE patients, but not in patients with other diseases or healthy controls. (A) Peripheral blood CD3 T cells prepared from 326 SLE patients were characterized by flow cytometry for surface-bound Ig (T-Ig)
Figure 2B:
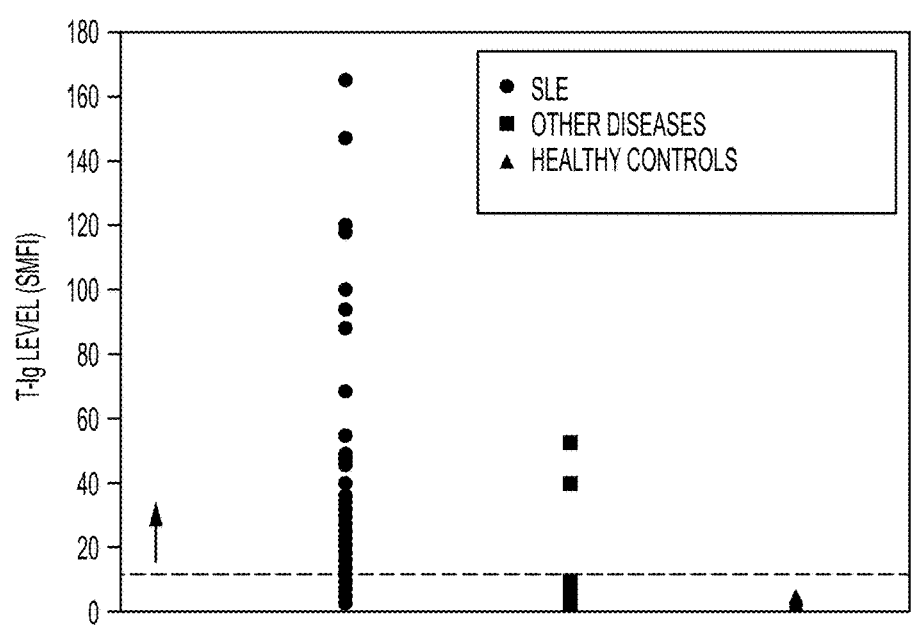

A mechanism responsible for T-C4d signatures should account for differential deposition of C4d on TCD4 versus TCD8 cells in some patients and the most likely explanation would be via autoantibodies specific for TCD4 versus TCD8 cells. This was investigated by flow cytometric analysis to examine and correlate the presence of C4d (T-C4d) and immunoglobulin (T-Ig) on the surface of T cells in patients with SLE. The results demonstrated that T cells from a significant fraction (~30%) of the SLE patient cohort were indeed decorated simultaneously with both C4d and Ig at the study visit (FIG. 2A). Considerable changes in T-C4d/T-Ig phenotype and levels within each individual patient were noted. A good correlation between T-C4d and T-Ig levels were noted in some, but not all patients. The inset within each histogram shows the corresponding correlation analysis. Blue columns: T-C4d; Purple columns: T-Ig. The remainder of SLE patients were either single positive for either C4d or Ig, or they were double negatives. In comparison, T cells of patients with other diseases and healthy controls were negative for both surface-bound Ig and C4d (FIG. 2B; data shown only for T-Ig). Of the 185 patients with other autoimmune diseases, only two patients, both with Sjögren's Syndrome, had significantly elevated levels of Ig present on the surface of their T cells. One of those two patients also had significantly elevated T-C4d levels.

Figure 2C:
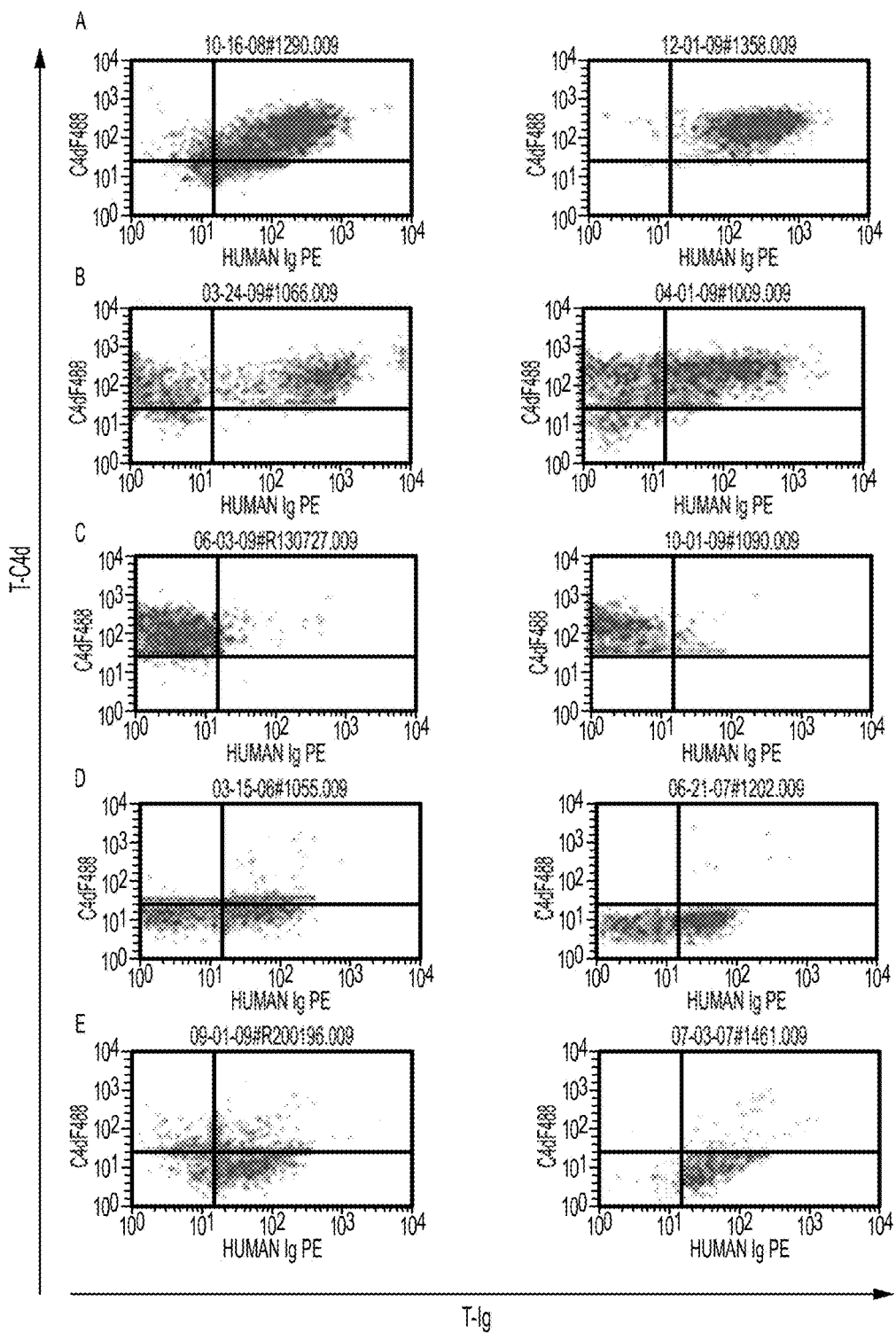

At any given time, T cells bearing both C4d and Ig (FIG. 2C, panel a), C4d alone (FIG. 2C, panel c), or Ig alone (FIG. 2C, panel e) could be detected in different SLE patients. Concomitant or individual presence of C4d and Ig on T cells in different patients and on T cell subsets in the same patients were noted. In some cases, distinct subpopulations of T cells bearing different levels of Ig and C4d could be detected simultaneously within the same patient (FIG. 2C, panels b and d). This latter finding suggested that these subpopulations may represent cells in transition from one stage to the next in a dynamic Ig/C4d binding process.

A selected group of SLE patients were followed and the presence of C4d and Ig on their T cells was examined periodically over time ranging from 9 to 33 months. As shown in FIG. 3A, among individual patients, both the levels of T-C4d and T-Ig, as well as the frequencies and ratios of T cells bearing C4d and/or Ig varied considerably over time. In some patients, T-C4d and T-Ig levels were strongly correlated throughout all study visits (e.g., patient #SLE 102763, $R^2$=0.7063; patient #SLE 101592, $R^2$=0.9551). However, in some patients, a general correlation between T-C4d and T-Ig levels was limited to a subset of the study visits (e.g., visits 1, 3, and 5 of patient #SEL102326). These results further suggest a dynamic Ig/C4d binding process that may vary among individual patients.

Furthermore, it was noted that the presence of surface-bound Ig on a specific subset of T cells correlated with increased levels of C4d on that particular T cell subpopulation. For example, selectively higher T-C4d levels on TCD4 cells corresponded with increased T-Ig levels selectively on TCD4 cells in a given patient (FIG. 3B, panels a and b), and vice versa (FIG. 3B, panels c and d). Note that when higher levels of Ig were detected on TCD4 cells than TCD8 cells in some patients (panel a), higher levels of C4d were also detected on TCD4 cells than on TCD8 cells (panel b). Similar correlations between increased levels of C4d (panel c) and Ig levels (panel d) were observed for TCD8 cells. These observations suggested a causal link between the binding of Ig and the deposition of C4d on T cells in SLE patients, most likely through activation of the classical complement pathway.

Example 4

The T-C4d Phenotype can be Transferred by Plasma from SLE Patients

Because Ig and C4d were detected simultaneously on the surface of circulating T cells of some SLE patients, a model was hypothesized in which binding of specific anti-T autoantibodies may activate the complement system and generate C4d that deposits onto the surface of these cells. Therefore, it was investigated whether the plasma of SLE patients can bind and "transfer" the T-C4d phenotype to normal T cells in vitro. Different plasma samples derived from the study cohort of SLE patients, patients with other diseases, and healthy controls were tested against T cells isolated from either healthy individuals or SLE patients who had negligible levels of T-C4d. T cells within the treated cell populations were analyzed by flow cytometry. As shown representatively in FIG. 4, normal T cells that were T-C4d negative (panel A) acquired significant levels of C4d on their surface after being treated with the plasma prepared from donor SLE patients who were known to have elevated T-C4d and T-Ig levels (panels B1 and C1). The patterns of T-C4d generated on the healthy recipient cells were remarkably similar to those present on the lupus donor cells in each experiment. In comparison, the plasma of a healthy control was not capable of generating C4d deposition on normal T cells (panel D1). Note the high levels of C4d deposited on cell surfaces after treatment with T-C4d+ SLE plasma and Ig, but not the healthy control plasma and Ig. The results have consistently shown that only the plasma of SLE patient donors who exhibited the elevated T-Ig/T-C4d phenotype, but not the plasma of SLE patients who exhibited the low T-Ig/T-C4d phenotype or the plasma of healthy controls, can transfer the T-C4d phenotype onto normal T cells. Transfer of the TC4d phenotype with plasma from lupus patients does not lead to generation of C5b-9 or to a significant decrease in cell numbers (data not shown).

Example 5

The T-C4d Phenotype can be Transferred by Immunoglobulin of SLE Patients

The phenotype transfer experiment was performed using Ig purified from the plasma of SLE patients. The results demonstrated that Ig purified from the plasma of SLE patients with high T-C4d levels were capable of transferring the T-C4d phenotype to normal T cells in vitro (FIG. 4, panels B2 and C2; cf. FIG. 4A). Ig purified from either healthy controls (FIG. 4, panel D2) or from SLE patients with negligible T-C4d levels (not shown) could not transfer the T-C4d signature. Equal concentrations of IgM, as compared with IgG, were more effective in generating the T-C4d signature, supporting a mechanistic role of classical complement pathway activation (FIG. 5A), in which IgM is a much more potent activator of the classical complement pathway as compared to IgG and is therefore much more effective in generating T-C4d on the cell surface after binding. Depletion of Ig from donor SLE plasma completely abolished its capacity to induce complement activation and C4d binding to T cells in vitro (FIG. 5B). Moreover, this capacity of the SLE plasma was significantly decreased if the potential lymphocyte-reactive humoral factors were removed by preincubation of the plasma with lymphocytes (FIG. 5B). Absorption with human platelets or fibroblasts had no effect (not shown). These results support the hypothesis that T-C4d signatures in patients with SLE are generated by anti-T cell and -T cell subset autoantibodies.

Example 6

Comparison Among SLE, Other Disease (OD) and Healthy Controls (HC)

Additional analyses were performed using the patient data as described below (Table 2). Continuous data were reported as mean±standard deviation (SD) and median and interquartile range (IQR), stratified by SLE, OD and HC. Analysis of variance (ANOVA) was used test the overall difference among three groups. Post hoc tests were used to provide the information on the pairwise comparisons. The sensitivity and specificity of CB-CAP biomarkers was determined in SLE subjects by using OD and HC patients, respectively. Receiver operating curves (ROCs) were used as appropriate for each of the markers and also the subsets.

TABLE 2

CB-CAP Panel Comparison Among SLE, Other Disease (OD) and Healthy Controls (HC)

| Disease | Variable | Mean | Std Dev | Median | 25th Pctl | 75th Pctl |
|---|---|---|---|---|---|---|
| HC | TIg | 0.5487500 | 1.2508340 | 0.1700000 | 0.0350000 | 0.5300000 |
| (n = 48) | TC4d | 1.4429167 | 1.0791426 | 1.3300000 | 0.5900000 | 1.9400000 |
|  | ECR1 | 12.5 | 5.6 | 12.6 | 8.2 | 16.8 |
|  | EC4d | 3.7488889 | 2.6261406 | 2.9300000 | 2.2300000 | 4.2900000 |
|  | PC4d | 0.5611111 | 1.1148751 | 0.1300000 | 0 | 0.3900000 |
|  | RC4d | 0.8920000 | 0.9510965 | 0.4600000 | 0.2600000 | 1.3800000 |
|  | BC4d | 9.0608696 | 6.8805636 | 6.9000000 | 4.5100000 | 10.2700000 |
|  | MC4d | 3.5850000 | 3.8248850 | 2.2900000 | 1.2800000 | 4.4400000 |
|  | GC4d | 0.6982609 | 0.6792947 | 0.5250000 | 0.2000000 | 1.0800000 |
| OD | TIg | 1.2831892 | 4.9232849 | 0.1700000 | 0 | 0.8000000 |
| (n = 185) | TC4d | 3.2357297 | 9.3510174 | 1.8500000 | 1.0900000 | 2.9200000 |
|  | ECr1 | 8.9911377 | 4.2039069 | 8.3500000 | 5.9900000 | 12.1600000 |
|  | EC4d | 5.1518452 | 4.2632467 | 3.8800000 | 2.7950000 | 5.6300000 |
|  | PC4d | 1.0604819 | 3.2516897 | 0.4600000 | 0.1700000 | 0.8200000 |
|  | RC4d | 3.0418405 | 7.3285795 | 1.2100000 | 0.6300000 | 1.8300000 |
|  | BC4d | 18.6081143 | 38.3786562 | 9.8800000 | 6.8000000 | 16.9200000 |
|  | MC4d | 3.9804545 | 7.2825194 | 2.0700000 | 1.4450000 | 3.6750000 |
|  | GC4d | 1.2422727 | 4.1408444 | 0.5250000 | 0.2900000 | 0.9000000 |
| SLE | TIg | 12.7297908 | 34.3706459 | 1.8000000 | 0.4200000 | 9.2800000 |
| (n = 325) | TC4d | 18.9777231 | 37.0139756 | 4.6800000 | 1.9600000 | 18.1200000 |
|  | ECr1 | 7.9572635 | 4.5400761 | 7.2500000 | 4.5300000 | 10.0050000 |
|  | EC4d | 12.5164189 | 19.2377533 | 6.8600000 | 4.0200000 | 12.6600000 |
|  | PC4d | 3.3771769 | 8.7511549 | 0.8200000 | 0.3700000 | 2.1600000 |
|  | RC4d | 7.4662324 | 17.8042195 | 2.0750000 | 1.0100000 | 5.6650000 |
|  | BC4d | 54.8311429 | 77.7344434 | 28.4500000 | 12.4700000 | 62.3900000 |
|  | MC4d | 11.6691304 | 25.4648764 | 4.5800000 | 2.3300000 | 9.2900000 |
|  | GC4d | 3.1526087 | 7.8589359 | 1.1500000 | 0.5600000 | 2.6200000 |

TABLE 3

ANOVA and Post Hoc Analysis of T-Ig and CB-CAP Assays

| | Overall comparison | Pair-wise comparison |
|---|---|---|
| T-Ig | <0.001 | SLE vs OD: <0.001 |
| | | SLE vs HC: <0.001 |
| TC4d | <0.001 | SLE vs OD: <0.001 |
| | | SLE vs HC: <0.001 |
| | | OD vs HC: 0.006 |
| ECR1 | <0.001 | SLE vs OD: 0.008 |
| | | SLE vs HC: <0.001 |
| | | OD vs HC: <0.001 |
| EC4d | <0.001 | SLE vs OD: <0.001 |
| | | SLE vs HC: <0.001 |
| | | OD vs HC: 0.012 |
| PC4d | <0.001 | SLE vs OD: <0.001 |
| | | SLE vs HC: <0.001 |
| | | OD vs HC: <0.001 |
| RC4d | <0.001 | SLE vs OD: <0.001 |
| | | SLE vs HC: <0.001 |
| | | OD vs HC: 0.002 |
| BC4d | <0.001 | SLE vs OD: <0.001 |
| | | SLE vs HC: <0.001 |
| | | OD vs HC: 0.001 |
| MC4d | <0.001 | SLE vs OD: <0.001 |
| | | SLE vs HC: <0.001 |
| GC4d | <0.001 | SLE vs OD: <0.001 |
| | | SLE vs HC: <0.001 |

Table 4 shows the sensitivity for SLE and specificity against Other Disease (OD) or Healthy Control (HC) according to T-Ig positivity and each individual CB-CAP biomarker positivity (positivity was defined as above the maximum value in HC, so specificity against HC was 100%).

TABLE 4

Diagnostic Performance of T-Ig and Individual CB-CAP Assays

| | Sensitivity for SLE | Specificity against OD | Specificity against HC |
|---|---|---|---|
| T-Ig | 33.2% (108/325) | 98.4% (182/185) | 100% (48/48) |
| TC4d | 48% (156/325) | 91.9% (170/185) | 100% (48/48) |
| ECR1 (n = 508) | 13.5% (40/296) | 91.0% (152/167) | 100% (45/45)) |
| EC4d (n = 509) | 22.3% (66/296) | 94.6% (159/159) | 100% (45/45) |
| PC4d (n = 505) | 12.6% (37/294) | 97.6% (162/166) | 100% (45/45) |
| RC4d (n = 492) | 29.6% (84/284) | 90.2% (147/163) | 100% (45/45) |
| BC4d (n = 536) | 44.8% (141/315) | 91.4% (160/175) | 100% (46/46) |
| MC4d (n = 544) | 12.7% (41/322) | 97.2% (171/176) | 100% (46/46) |
| GC4d (n = 544) | 20.2% (65/322) | 93.4% (165/176) | 100% (46/46) |

To find the biomarkers or their combinations that increase sensitivity but maintain highest specificity, the sensitivity/specificity in T-Ig negative subjects was first determined with each individual CB-CAP biomarker. It was found that TC4d was the best, increasing overall sensitivity for SLE from 33.2% (Table 4) to 55.1%. (Table 5)

TABLE 5

Improvement of Diagnostic Performance Among T-Ig-Negative Subjects by Addition of CB-CAP Assays and Overall Performance

|  | T-Ig negative | | | Overall | | |
|---|---|---|---|---|---|---|
|  | Sensitivity for SLE | Specificity against OD | Specificity against HC | Sensitivity for SLE | Specificity against OD | Specificity against HC |
| TC4d | 32.7 | 92.3 | 100 | 55.1 | 90.8 | 100 |
| ECR1 | 10.7 | 90.9 | 100 | 42.3 | 89.3 | 100 |
| EC4d | 13.2 | 94.6 | 100 | 43.9 | 92.9 | 100 |
| PC4d | 7.6 | 97.6 | 100 | 40.3 | 95.8 | 100 |
| RC4d | 22.2 | 90.1 | 100 | 50.0 | 88.4 | 100 |
| BC4d | 28.7 | 91.9 | 100 | 52.7 | 90.3 | 100 |
| MC4d | 7.9 | 97.7 | 100 | 38.8 | 96.0 | 100 |
| GC4d | 13.6 | 93.6 | 100 | 42.6 | 92.1 | 100 |

Sequentially, the next best biomarker among individuals with both negative T-Ig and TC4d was identified. As shown in Table 6, it was found that combining T-Ig and TC4d would increase overall sensitivity from 33.2% to 55.1%, while keeping near perfect specificity against other disease and healthy controls, 90.8% and 100%, respectively. Adding B-C4d to TC4d could further increase sensitivity for SLE to 61.1%, however overall specificity against OD decreased to 86.4%.

TABLE 6

Improvement of Diagnostic Performance by Stepwise Addition of Multiple CB-CAP Assays

|  | Overall | | |
|---|---|---|---|
|  | Sensitivity for SLE | Specificity against OD | Specificity against HC |
| T-Ig only | 33.2 | 98.4 | 100 |
| +TC4d | 55.1 | 90.8 | 100 |
| +BC4d | 61.1 | 86.4 | 100 |
| +RC4d | 67.7 | 80.2 | 100 |
| +EC4d | 68.4 | 79.1 | 100 |
| +Any other | 72.3 | 72.8 | 100 |

+indicates sequentially adding from top to bottom of the column. For example, +TC4d means the combination of T-Ig and TC4d.

The data were plotted using receiver operating characteristic (ROC) curves, which are graphical plots that illustrate the performance of a binary classifier system as its discrimination threshold is varied. These analyses demonstrate the added value of T-Ig combined with CB-CAP assays as diagnostic tools.

FIG. 6A shows ROC comparisons in discriminating SLE and healthy controls, with all biomarkers. ROC analysis comparing SLE and healthy controls revealed that BC4d (AUC=0.853) and TC4d (AUC=0.840) were the best predictors followed by RC4d (AUC=0.80) and EC4d (AUC=0.80). This was consistent with the results shown above in Table 6.

FIG. 6B shows ROC comparisons in discriminating SLE and healthy controls, with a subset of CB-CAP biomarkers (TC4d, EC4d, RC4d and BC4d).

FIG. 7A shows ROC comparisons in discriminating SLE and other disease.

ROC analysis comparing SLE and other disease revealed that BC4d (AUC=0.755) and TC4d (AUC=0.750) were the best predictors. Compared to T-Ig only (0.76), the overall ROC increased from 0.76 to 0.80, and this difference approached statistical significance (p=0.07).

FIG. 7B shows ROC comparisons in discriminating SLE and other disease, with a subset of CB-CAP biomarkers (TC4d, EC4d, RC4d and BC4d).

The features and functions described above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

Where features or aspects of the invention are described in terms of a Markush group or other grouping of alternatives, those skilled in the art will recognized that the invention is also thereby described in terms of any individual member or subgroup of members of the Markush group or other group.

Unless indicated to the contrary, all numerical ranges described herein include all combinations and subcombinations of ranges and specific integers encompassed therein. Such ranges are also within the scope of the described invention.

All references cited herein are incorporated by reference herein in their entireties.

We claim:

1. A method of specifically diagnosing systemic lupus erythematosus in an individual distinct from a non-systemic lupus erythematosus inflammatory condition, which comprises, obtaining a blood sample from the individual;

incubating the blood sample in vitro, wherein incubation results in autoantibodies in the sample being in stable association with a surface of a T lymphocyte in the sample, wherein C4d is bound to a surface of the T lymphocyte;

quantitating a level of the individual's autoantibodies deposited on or in contact with a surface of a TC4d lymphocyte in the sample;

comparing the level of autoantibodies in the blood sample from the individual with a level of autoantibodies deposited on or in contact with a surface of a control T lymphocyte;

quantitating a level of a diagnostic biomarker of systemic lupus erythematosus deposited on or in contact with a surface of a T lymphocyte in the sample, wherein the diagnostic biomarker is C4d; and comparing the level of TC4d diagnostic biomarker in the blood sample from the individual with a level of the diagnostic biomarker deposited on or in contact with a surface of a control T lymphocyte;

wherein an increased level of autoantibodies deposited on or in contact with the surface of a TC4d lymphocyte and an increased level of the TC4d diagnostic biomarker in the blood sample from the individual as compared to the levels for the control T lymphocyte identifies systemic lupus erythematosus in the individual.

2. The method of claim 1 wherein the level of the individual's autoantibodies deposited on or in contact with the surface of the T lymphocyte is measured from a population of peripheral blood mononuclear cells obtained from the blood sample.

3. The method of claim 2 wherein the T lymphocyte is represented in the sample by at least one T lymphocyte cell type selected from the group consisting of a $CD4^+$ Th1 lymphocyte cell, a $CD4^+$ Th2 lymphocyte cell and a $CD8^+$ cytotoxic lymphocyte cell.

4. The method of claim 3 wherein the T lymphocyte is a $CD4^+$ Th1 lymphocyte cell.

5. The method of claim 3 wherein the T lymphocyte is a $CD4^+$ Th2 lymphocyte cell.

6. The method of claim 3 wherein the T lymphocyte is a $CD8^+$ cytotoxic lymphocyte cell.

7. The method of claim 1 which comprises:
obtaining a blood sample containing white blood cells from the individual;
incubating the blood sample in vitro, wherein incubation results in autoantibodies in the sample being in stable association with a surface of a T lymphocyte in the sample, wherein C4d is bound to a surface of the T lymphocyte;
isolating a peripheral blood mononuclear cell population from the blood sample;
incubating the peripheral blood mononuclear cell population with a detectable reagent which specifically binds to an autoantibody bound to the cell surface of a TC4d lymphocyte within the peripheral blood mononuclear cell population, forming a T lymphocyte-autoantibody-detectable reagent complex; and
measuring the level of the T lymphocyte-autoantibody-detectable reagent complex.

8. The method of claim 7 wherein the T lymphocyte-autoantibody-detectable reagent complex is measured by flow cytometry.

9. The method of claim 7 which comprises:
comparing the level of the T cell-autoantibody-detectable reagent complex obtained from the individual with a level of a T lymphocyte-autoantibody-detectable reagent complex obtained from a control blood sample;
wherein an increase in the level of the T lymphocyte-autoantibody-detectable reagent complex measured from the individual's blood sample as compared to the control blood sample, and an increased level of TC4d in the sample, as compared to the control blood sample, identifies systemic lupus erythematosus in the individual.

10. The method of claim 7 wherein the detectable reagent is a fluorescently-labeled anti-human Ig antibody which is detectable by flow cytometry.

11. The method of claim 10 wherein the fluorescently-labeled anti-human Ig antibody is selected from the group consisting of a fluorescently-labeled anti-human IgG antibody and a fluorescently-labeled anti-human IgM antibody.

12. The method of claim 1, further comprising:
assaying a level of C4d bound to B lymphocytes (BC4d); and
comparing the level of BC4d in the blood sample from the individual with a level of BC4d in a blood sample from a healthy control,
wherein an increased level of autoantibodies deposited on or in contact with the surface of a TC4d lymphocyte and an increased level of TC4d in the blood sample from the individual as compared to the levels for the control T lymphocyte; combined with an increased level of BC4d in the sample from the individual as compared to the control sample, identifies systemic lupus erythematosus in the individual.

13. The method of claim 12 wherein the sensitivity of the method for systemic lupus erythematosus is at least 61.1% and the specificity against other diseases is at least 86.4%.

14. The method of claim 12, further comprising:
assaying a level of C4d bound to reticulocytes (RC4d); and
comparing the level of RC4d in the blood sample from the individual with a level of RC4d in a blood sample from a healthy control,
wherein an increased level of autoantibodies deposited on or in contact with the surface of a TC4d lymphocyte and an increased level of TC4d in the blood sample from the individual as compared to the levels for the control T lymphocyte; combined with increased levels of BC4d and RC4d in the sample from the individual as compared to the control sample, identifies systemic lupus erythematosus in the individual.

15. The method of claim 14 wherein the sensitivity of the method for systemic lupus erythematosus is at least 67.7% and the specificity against other diseases is at least 80.2%.

16. The method of claim 14, further comprising:
assaying a level of C4d bound to erythrocytes (EC4d); and
comparing the level of EC4d in the blood sample from the individual with a level of EC4d in a blood sample from a healthy control,
wherein an increased level of autoantibodies deposited on or in contact with the surface of a TC4d lymphocyte and an increased level of TC4d in the blood sample from the individual as compared to the levels for the control T lymphocyte; combined with an increased levels of BC4d, RC4d and EC4d in the sample from the individual as compared to the control sample, identifies systemic lupus erythematosus in the individual.

17. The method of claim 16 wherein the sensitivity of the method for systemic lupus erythematosus is at least 68.4% and the specificity against other diseases is at least 79.1%.

18. The method of claim 1 wherein the sensitivity of the method for systemic lupus erythematosus is at least 55.1%, and the specificity against other diseases is at least 90.8%.

19. A method of specifically monitoring the disease activity of systemic lupus erythematosus in an individual distinct from a non-systemic lupus erythematosus inflammatory condition, which comprises,
obtaining a blood sample from the individual;
incubating the blood sample in vitro, wherein incubation results in autoantibodies in the sample being in stable association with a surface of a T lymphocyte in the sample, wherein C4d is bound to a surface of the T lymphocyte;
quantitating a level of the individual's autoantibodies deposited on or in contact with a surface of a TC4d lymphocyte in the blood sample;
comparing the level of autoantibodies in the blood sample from the individual with a level of autoantibodies deposited on or in contact with a surface of a control T lymphocyte isolated from a blood sample obtained from the same individual at an earlier time;

quantitating a level of a diagnostic biomarker of systemic lupus erythematosus deposited on or in contact with a surface of a T lymphocyte in the sample, wherein the diagnostic biomarker is C4d; and comparing the level of TC4d diagnostic biomarker in the blood sample from the individual with a level of the diagnostic biomarker deposited on or in contact with a surface of a control T lymphocyte isolated from a blood sample obtained from the same individual at an earlier time;

wherein an increased level of autoantibodies deposited on or in contact with the surface of a TC4d lymphocyte and an increased level of TC4d in the sample as compared to the control sample obtained from the same individual at an earlier time indicates an increased level of systemic lupus erythematosus disease activity in the individual, and wherein a decreased level of autoantibodies deposited on or in contact with the surface of a TC4d lymphocyte and a decreased level of TC4d in the sample as compared to the control sample obtained from the same individual at an earlier time indicates a decreased level of systemic lupus erythematosus disease activity in the individual.

20. The method of claim 19, further comprising:

assaying a level of BC4d; and comparing the level of BC4d in the blood sample from the individual with a level of BC4d in a blood sample obtained from the individual at the earlier time, wherein an increased level of autoantibodies deposited on or in contact with the surface of a TC4d lymphocyte and an increased level of TC4d in the sample as compared to the control sample obtained from the same individual at an earlier time; combined with an increased level of BC4d in the sample as compared to the control sample obtained from the same individual at an earlier time, indicates an increased level of systemic lupus erythematosus disease activity in the individual, and wherein a decreased level of autoantibodies deposited on or in contact with the surface of a TC4d lymphocyte and a decreased level of TC4d in the sample as compared to the control sample obtained from the same individual at an earlier time; combined with a decreased level of BC4d in the sample as compared to the control sample obtained from the same individual at an earlier time, indicates a decreased level of systemic lupus erythematosus disease activity in the individual.

21. The method of claim 20, further comprising:

assaying a level of RC4d; and comparing the level of RC4d in the blood sample from the individual with a level of RC4d in a blood sample obtained from the individual at the earlier time, wherein an increased level of autoantibodies deposited on or in contact with the surface of a TC4d lymphocyte and an increased level of TC4d in the sample as compared to the control sample obtained from the same individual at an earlier time; combined with increased levels of BC4d and RC4d in the sample as compared to the sample obtained from the same individual at an earlier time, indicates an increased level of systemic lupus erythematosus disease activity in the individual, and wherein a decreased level of autoantibodies deposited on or in contact with the surface of a TC4d lymphocyte and a decreased level of TC4d in the sample as compared to the control sample obtained from the same individual at an earlier time; combined with decreased levels of BC4d and RC4d in the sample as compared to the sample obtained from the same individual at an earlier time, indicates a decreased level of systemic lupus erythematosus disease activity in the individual.

22. The method of claim 19, further comprising:

assaying a level for each of EC4d, RC4d, and BC4d, and comparing the level for each of EC4d, RC4d, and BC4d in the blood sample from the individual with a level for each of EC4d, RC4d, and BC4d in a blood sample obtained from the same individual at an earlier time, wherein an increased level of autoantibodies deposited on or in contact with the surface of a TC4d lymphocyte and an increased level of TC4d in the sample as compared to the sample obtained from the same individual at an earlier time; combined with an increased level for each of EC4d, RC4d, and BC4d in the sample as compared to the sample obtained from the same individual at an earlier time, indicates an increased level of systemic lupus erythematosus disease activity in the individual, and wherein a decreased level of autoantibodies deposited on or in contact with the surface of a TC4d lymphocyte and a decreased level of TC4d in the sample as compared to the sample obtained from the same individual at an earlier time; combined with a decreased level for each of EC4d, RC4d, and BC4d in the sample as compared to the sample obtained from the same individual at an earlier time, indicates a decreased level of systemic lupus erythematosus disease activity in the individual.

* * * * *